US007758867B2

(12) United States Patent
Seong et al.

(10) Patent No.: US 7,758,867 B2
(45) Date of Patent: Jul. 20, 2010

(54) ATTENUATED INFLUENZA VIRUS AND A LIVE VACCINE COMPRISING THE SAME

(75) Inventors: Baik Lin Seong, Seoul (KR); Kwang Hee Lee, Gyeonggido (KR); Sang Uk Seo, Seoul (KR)

(73) Assignee: Biotrion Co., Ltd., Seongnam-Si, Gyeonggi-Do (KR)

( * ) Notice: Subject to any disclaimer, the term of this patent is extended or adjusted under 35 U.S.C. 154(b) by 0 days.

(21) Appl. No.: 11/764,532

(22) Filed: Jun. 18, 2007

(65) Prior Publication Data

US 2008/0311153 A1 Dec. 18, 2008

Related U.S. Application Data

(60) Provisional application No. 60/944,256, filed on Jun. 15, 2007.

(51) Int. Cl.

| | |
|---|---|
| ***A61K 39/145*** | (2006.01) |
| ***A61K 39/12*** | (2006.01) |
| ***A61K 39/38*** | (2006.01) |
| ***A61K 39/295*** | (2006.01) |
| ***A01N 63/00*** | (2006.01) |
| ***C12P 19/34*** | (2006.01) |

(52) U.S. Cl. .............. 424/206.1; 424/209.1; 424/205.1; 424/184.1; 424/202.1; 424/93.6; 435/91.33

(58) Field of Classification Search ....................... None
See application file for complete search history.

(56) References Cited

U.S. PATENT DOCUMENTS 6,344,354 B1 * 2/2002 Webster et al. ........... 435/235.1

OTHER PUBLICATIONS

Lee et al., Characterization of live influenza vaccine donor strain derived from cold-adaptation of X-31 virus, 2006, Vaccine, vol. 24, pp. 1966-1974.*

Genbank accession, DQ874873, Influenza A Virus (A/X-31 (H3N2)) polymerase basic protein 2 (PB2), 2008.*

Genbank accession, DQ874874, Influenza A Virus (A/X-31 (H3N2)) polymerase basic protein 1 (PB1), 2008.*

Genbank accession, DQ874875, Influenza A Virus (A/X-31 (H3N2)) polymerase acidic protein (PA), 2008.*

Genbank accession, DQ874877, Influenza A Virus (A/X-31 (H3N2)) nucleocapsid protein (NP), 2008.*

Genbank accession, DQ874879, Influenza A Virus (A/X-31 (H3N2)) matrix protein 2 and matrix protein 1 (M), 2008.*

Genbank accession, DQ874880, Influenza A Virus (A/X-31 (H3N2)) nonstructural protein 2 and nonstructural protein 1 (NS), 2008.*

Yannarell et al., Factors affecting the yield of cold-adapted influenza virus vaccine, 1997, Journal of Virological Methods, vol. 64, pp. 161-169.*

Genbank Accession # DQ487337, Jun. 2, 2006, <<Influenza A virus (A/Panama/2007/1999 (H3N2)) segment 6, complete sequence.*

Genbank Accession # DQ487340, Jun. 2, 2006, <<Influenza A virus (A/Panama/2007/1999 (H3N2)) segment 4, complete sequence.*

Seo et al., Immediate and broad-spectrum protection against heterologous and heterotypic lethal challenge in mice by live influenza vaccine, 2007, Vaccine, No. 25, pp. 8067-8076.*

* cited by examiner

*Primary Examiner*—Patrick J Nolan
*Assistant Examiner*—Benjamin P Blumel
(74) *Attorney, Agent, or Firm*—Lucas & Mercanti, LLP

(57) ABSTRACT

The present invention relates to an isolated attenuated influenza virus strain and a live vaccine comprising the same. The isolated attenuated influenza virus strain is prepared by cold-adaptation of a mother strain which carries 6 internal genomes of A/PR/8/34(H1N1) and two surface antigens HA and NA of A/Aichi/2/68(H3N2). The attenuated influenza virus strain and the live vaccine of the present invention are useful for prevention of seasonal influenza episodes and sudden outbreak of influenza pandemics of predicted or unknown identity, since they have safety, efficacy, high production yield, immediate protection against variety of influenza subtypes and prolonged protection against specific influenza subtype.

8 Claims, 11 Drawing Sheets

(A) HI for serum (B) EIA for serum IgG (C) EIA for sIgA in BAL (D) EIA for sIgA in nasal wash (E) Protective efficacy (challenge dose: A/NC $8.0 \times 10^6$ TCID$_{50}$/mouse = 100 MID$_{50}$)

ATTENUATED INFLUENZA VIRUS AND A LIVE VACCINE COMPRISING THE SAME

CROSS REFERENCE TO RELATED APPLICATIONS

This patent application claims the benefit of U.S. Provisional Patent Application Ser. No. 60/944,256, filed Jun. 15, 2007, the contents of which are incorporated by reference herein in their entirety.

FIELD OF THE INVENTION

The present invention relates to an attenuated influenza virus and a live vaccine comprising the same.

BACKGROUND OF THE INVENTION

Influenza A viruses are responsible for the major pandemics of influenza in the last century and are also the causative agents for most of the annual outbreaks of epidemic influenza. The influenza virus is an enveloped virus belonging to the family of the Orthomyxoviridae. Within the envelope, the virus carries eight different RNA segments. There are many different influenza strains, and based on distinctive immunogenic properties, the virus are classified into three types: influenza A, B and C viruses (Influenza. Kilbourne E D ed. Plenum press 1987).

Influenza virus carries at least two different surface glycoprotein antigens on the external envelop, hemagglutinin (HA) trimer, consisting of three individual HA monomers, and the neuraminidase (NA) that exists as tetramer. Both HA and NA plays pivotal role during infection into susceptible cells. There are very immunogenic and elicits specific antibody responses during infection.

There are many different influenza A virus subtypes, differing in the nature of the HA and NA glycoproteins on their surface. Sixteen HAs (H1 to H16) and nine NAs (N1 to N9) have been identified. Among these, H1, H2 and H3 virus subtypes have been identified in humans, specifically the H1N1, H2N2 and H3N2 viruses corresponding to the three major pandemics of the last century (Fields Virology $4^{th}$, ed. Fields B N, Knipe D M and Howly P M eds, 1489, 2001). Virus subtypes are distinguishable serologically, which means that antibodies to one subtype do not properly react with another subtype. Besides, humans, influenza viruses infect variety of hosts including swine, avian and equestrian species. Among these, aquatic birds appear to serve as a major reservoir of influenza A viruses; indeed, all human influenza virus subtypes circulate also in these wild birds. During resent outbreaks of avian influenza, there have been occasional transmissions of H5N1, H7N7 and H9N2 viruses to humans (*Proc. Natl. Acad. Sci.* USA 101, 8156-8161, 2004).

Besides influenza A subtypes, influenza B virus also infects humans especially very young children. Serologically, influenza B virus is clearly distinct from two different subtypes of influenza A viruses (A/H1N1 and A/H3N2) that currently circulates globally. For this reason, current influenza vaccine stipulates the use of three different components (A/H1N1, A/3N2 and B virus) as trivalent vaccine formula.

Because of high mutation rate of the RNA genome, different strains emerge almost every year that cause annual influenza epidemics. Antigenic drift involves minor changes in the RA, NA and possibly also other viral antigen, that occur due to mutations in the viral genome, resulting in amino acid substitution in antigenic sites. These changes may render the new strain different enough to at least partially avoid the immunity induced by previous strains.

Since influenza virus genomes are segmented, influenza virus frequently undergoes more drastic changes 'antigenic shift' by genetic reassortment between different viruses. This means that a virus with a new HA (and NA) are introduced into the human population. Especially among those who are immunologically naïve, the infection would spread rapidly and cause high morbidity and mortality among the entire population, including young healthy people. Human population has experienced at least three major influenza pandemics in the 20th century. The Spanish influenza (caused by an H1N1, influenza A virus) in 1918 resulted in the death to 20 to 50 million worldwide. The sequence of the virus shows that similar mutations were also observed in the recent H5N1 avian influenza isolates that infects humans (*Nature* 437, 889-93, 2005). Other pandemics occurred in 1957 (Asian flu, 112N2) and 1968 (Hong Kong flu, H3N2) with a total number of deaths of approximately 2 million. Moreover, there are numerous reports on human infection by avian influenza viruses (including H5N1, H7N7 and H9N2 viruses) in the past several years. The current information supports the concept that new pandemic influenza is derived from avian virus reservoirs. Avian influenza viruses may be directly transmitted to humans, which probably occurred in the case of the 1918 Spanish flu virus. The possibility of direct transmission of an avian influenza virus to humans became evident for the first time during the H5N1 outbreak in Hong Kong in 1997.

Recently, influenza B viruses have been isolated from animals, demonstrating that influenza B viruses are not restricted to humans and raising concerns about the potential for influenza B viruses to emerge with new antigenic properties. Moreover, influenza B virus infection has been associated with acute necrotizing encephalopathy (ANE) and influenza B-associated encephalitis (IBAE) and neurological sequela.

Vaccination remains the cornerstone of influenza prevention, and currently, trivalent vaccine containing three different influenza surface antigens (A/H1N1, A/H3N2 and B virus) are being used. Antigenic drift of established human virus subtypes requires regular update of the composition of the annual influenza vaccine necessitating annual vaccination. For this reason, current influenza vaccine stipulates the use of three different components as trivalent vaccine formula. In addition, because of potential circulation among humans of avian influenza viruses such as H5N1, H9N2 or H7N7, tetravalent and even multivalent vaccine can also be used for cross-protection against various influenza viruses.

There are several potential strategies for the development of vaccines to protect humans against influenza viruses, including (1) inactivated vaccine; (2) subunit vaccine that uses purified HA and NA components; and (3) live attenuated vaccines. Live attenuated vaccines generally provide better protection than inactivated on subunits vaccines as exemplified by previous developed A/Ann Arbor/6/60 (AA) (H2N2) virus or A/Lenhngrad/134/47/57 (H2N2) (*Antiviral Res.* 1, 339-365, 1981). The live vaccine stimulates the secretion of IgA class antibodies in the respiratory tract and inactivates the infecting virus on the infection site providing an on-site protection. (*New Eng J Med.* 338, 1405-1412, 1998*; Vaccine* 18, 82-88, 2000)

Classically, live attenuated vaccine has been developed through cold adaptation of infectious viruses (*Antiviral Res.* 1, 339-365, 1981). Using this virus as backbone strain, recombinant virus could be generated by annual reassortment between the ca virus and seasonal virulent influenza virus. The reassortant virus—carrying the surface antigens (RA ad NA) derived from the virulent strain and the six internal RNAs inherited from the ca virus—is immunologically identical to virulent strain but as attenuated as the parental ca virus. The virus, when given to human preferably through nasal route, does not cause virulent symptoms, and yet would induce specific protective immune response. Influenza vaccines are generally produced from virus grown on embryonated chicken eggs.

Ideally, a live vaccine should be both safe, effective in providing protection and cost-effective in production. For safety, the vaccine should be sufficiently attenuated and would not cause clinical symptom even at high dose of vaccination. For effective protection, the vaccine, even at low dose of vaccination, should be immunogenic enough to provide sufficient protection from virulent infection. Moreover, the vaccine strain must retain good growth property in embryonated eggs to reduce the production cost. The current global production capacity of egg-based influenza vaccine is very limited, with only 0.3 to 0.5 billion doses annually, which covers only 6-10% of global population. In time of pandemics (H5N1 avian influenza, for example), the whole population is expected to suffer from the shortage of vaccine supply. Therefore, high-titre production of in embryonated eggs is especially important for influenza vaccine (WHO/CDS/CSR/RMD/2004.8).

In practice, however, it is usually difficult to generate a vaccine strain that satisfies all three requirements-safety, efficacy and the cost-effectiveness. This difficulty is inherently associated with the process of attenuation and the use of live vaccine. Usually, attenuation (providing safety) results in poor growth (at the expense of cost-effectiveness), and renders the virus less immunogenic (requiring high dose of vaccination). In addition, since there are many variants of influenza viruses, matching of surface antigens (HA and NA) between the vaccine and the virulent virus is really important for protection. Therefore, prediction of influenza, strains should be made well ahead of actual circulation of seasonal influenza in winter time. If prediction fails, the vaccine of that particular influenza season is not effective. Unfortunately, the current inactivated influenza vaccine relies on specific, delayed immune response and does not provide enough cross-protection to different subtypes of influenza viruses (*J Am Med Assoc* 253, 1136-1139, 1985). Moreover, the vaccine does not provide protection from immediate infection (within one to five days before infection, for example), and should be given well ahead of infection, preferably at least 24 weeks before infection, to provide good protection. In contrast to seasonal influenza, the outbreak of avian influenza infection cannot be predicted (*Cell* 124: 665-70, 2006). The current influenza vaccine therefore has intrinsic limitation in providing immediate protection against sudden influenza outbreaks with unknown identity.

As preparedness for newly emerging threat posed by avian influenza, WHO now recommends, in addition to stockpiling of antivirals, the development of pandemic vaccines suitable for mass immunization administered in non-invasive route (WHO/CDS/CSR/RMD/2004.8). Although vaccines and antiviral drugs constitute essential components for this purpose, they present intrinsic limitations as efficient control measures of pandemics: antivirals such as Tamiflu™ are usually effective only after infection whereas vaccines should be administered well ahead of infection, preferably at least 2 to 4 weeks before exposure to circulating viruses: Currently, there is no effective means for controlling immediate infection. This issue is important especially for avian influenza, where outbreak and the speed of spread among human population are unpredictable.

The limitation of the current influenza vaccine therefore calls for the development of novel vaccine and prophylactic strategies. Ideally, an efficient vaccine would provide both (1) broad-spectrum immediate prophylaxis against variety of influenza viruses of unknown identity, and (2) delayed but specific protection against circulating virus of which the identity has been predicted when used well ahead of infection, preferably 2-4 weeks before infection following generally recommended vaccination schedule.

Accordingly, the development of novel live influenza vaccine that addresses to all important issues: safety, efficacy, high production yield, immediate protection against variety of influenza subtypes and prolonged protection against specific influenza subtype is needed.

SUMMARY OF THE INVENTION

The present invention provides an isolated attenuated influenza virus strain prepared by cold-adaptation of a mother strain which carries 6 internal genomes of A/PR/8/34(H1N1) and two surface antigens HA and NA of A/Aichi/2/68 (H3N2). In a preferred embodiment of the present invention, the attenuated influenza virus strain preferably comprises one or more RNA genomes having nucleotide sequences selected from a group consisting of SEQ ID NO: 1 to 6 but not limited thereto. In more preferred embodiment, the attenuated influenza virus strain is PT-IV-01 deposited at Korea Culture Center of Microorganisms (KCCM) under accession number KCCM 10854P.

In an embodiment of the present invention, a live vaccine comprising the attenuated influenza virus strain as an effective ingredient and at least one pharmaceutically acceptable carrier or excipient is provided.

In another embodiment of the present invention, a use of the attenuated influenza virus strain in the manufacture of a live vaccine for protecting infection of influenza viruses. In a preferred embodiment, the live vaccine is a trivalent vaccine including two human influenza A subtypes and one influenza B type. In a more preferred embodiment, the live vaccine is a multivalent vaccine formulation including more than two human influenza A subtypes and one influenza B type and one avian influenza subtype.

In still another embodiment of the present invention, a method for early protection against one or more influenza viruses having a specific or unknown surface antigens comprising administrating a pharmaceutically effective amount of the live vaccine of the present invention to a person in need of protection against the influenza viruses is also provided. In a preferred embodiment, the early protection is a protecting influenza infection of host at or after about one day from vaccination. In another preferred embodiment, the influenza virus is a human influenza virus or an avian influenza virus. In a more preferred embodiment, the human influenza virus is human influenza virus A or B.

In another aspect, the present invention provides a reassortant influenza virus strain comprises (i) 6 RNA genomes which are originated from the attenuated influenza virus and contain internal genes of the influenza virus and (ii) 2 RNA genomes encoding HA and NA surface antigens of other virulent viruses. In a preferred embodiment, the reassortant influenza virus strain is PT-IV-01re prepared by mating PT-IV-01 and A/Panama/2007/99 (H3N2).

In another embodiment of the present invention, a live vaccine comprising the reassortant virus strain as an effective ingredient and at least one pharmaceutically acceptable carrier or excipient is provided.

In another embodiment of the present invention, a use of the reassortant influenza virus strain in the manufacture of a live vaccine for protecting infection of influenza viruses. In a preferred embodiment, the live vaccine is a trivalent vaccine including two human influenza A subtypes and one influenza B type. In a more preferred embodiment, the live vaccine is a multivalent vaccine formulation including more than two human influenza A subtypes and one influenza B type and one avian influenza subtype.

In still another embodiment of the present invention, a dual use of the reassortant influenza virus strain in early protection and long-term prolonged protection against currently circulating influenza viruses.

In a preferred embodiment, the early protection is a protecting influenza infection of host at or after about one day from vaccination. In a preferred embodiment, the long-term prolonged protection is a protection for more than a month. In a more preferred embodiment, the long-term prolonged protection is a protection up to between 6 months and one year. In another preferred embodiment, the influenza virus is a human influenza virus or an avian influenza virus. In a more preferred embodiment, the human influenza virus is a human influenza virus A or B.

In still another embodiment of the present invention, a method for early and long-term protecting against an influenza virus infection comprising administrating a pharmaceutically effective amount of the live vaccine of the present invention to a person in need of protection against the influenza virus is provided.

In still another embodiment of the present invention, a method of generating attenuated influenza strain comprising serially passing a mother strain which carries 6 internal genomes of A/PR/8/34(H1N1) and two surface antigens HA and NA of A/Aichi/2/68(H3N2) at progressively low temperature, initially at 30° C. and followed by 27° C. and 24° C. is provided.

In another aspect of the present invention, a live vaccine comprising the attenuated influenza virus strain and the reassortant influenza virus strain as pharmaceutically effective ingredients and at least one pharmaceutically acceptable carrier or excipient is provided.

The PT-IV-01 based vaccine is therefore useful for prevention of seasonal influenza episodes and sudden outbreak of influenza pandemics of predicted or unknown identity.

DETAILED DESCRIPTION OF THE INVENTION

Figure 1A:
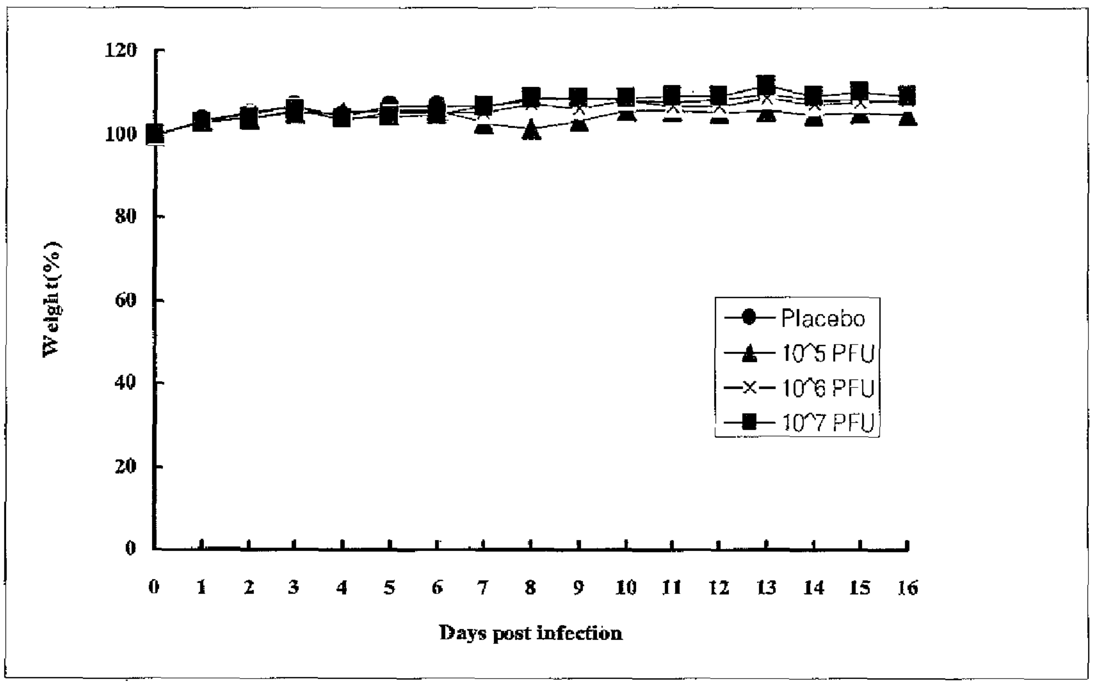
FIG. 1A is a graph showing effects of viral inoculation with PT-IV-01 on weight-loss in BALB/c mice. The PT-IV-01 virus was inoculated at different titers ($10^5$-$10^7$ PFU/mouse) and then weighted daily PBS inoculated control (●), inoculated with $10^5$ PFU/mouse (▲), inoculated with $10^6$ PFU/mouse (x) and inoculated with $10^7$ PFU/mouse (■).

The present invention provides an attenuated influenza virus strain prepared by cold-adaptation of a mother strain which carries 6 internal genomes of A/PR/8/34(H1N1) and two surface antigens HA and NA of A/Aichi/2/68(H3N2). In a preferred embodiment of the present invention, the attenuated influenza virus strain preferably comprises one or more RNA genomes having nucleotide sequences selected from a group consisting of SEQ ID NO: 1 to 6 but not limited thereto. In more preferred embodiment, the attenuated influenza virus strain is PT-IV-01 deposited at Korea Culture Center of Microorganisms (KCCM) under accession number KCCM 10854P.

In an embodiment of the present invention, a live vaccine comprising the attenuated influenza virus strain as an effective ingredient and at least one pharmaceutically acceptable carrier or excipient is provided.

In another embodiment of the present invention, a use of the attenuated influenza virus strain in the manufacture of a live vaccine for protecting infection of influenza viruses. In a preferred embodiment, the live vaccine is a trivalent vaccine including two human influenza A subtypes and one influenza B type.

In still another embodiment of the present invention, a method for early protection against one or more influenza viruses having a specific or unknown surface antigens comprising administrating pharmaceutically effective amount of the live vaccine of the present invention to a person in need of protection against the influenza viruses is also provided. In a preferred embodiment, the early protection is a protecting influenza infection of host at or after about one day from vaccination. In another preferred embodiment, the influenza virus is a human influenza virus or an avian influenza virus. In a more preferred embodiment, the human influenza virus is human influenza virus A or B.

In another aspect, the present invention provides a reassortant influenza virus strain comprises (i) 6 RNA genomes which are originated from the attenuated influenza virus and contain internal genes of the influenza virus and (ii) 2 RNA genomes encoding HA and NA surface antigens of other virulent viruses. In a preferred embodiment, the reassortant influenza virus strain is PT-IV-01re prepared by mating PT-IV-01 and A/Panama/2007/99 (H3N2).

In another embodiment of the present invention, a live vaccine comprising the reassortant virus strain as an effective ingredient and at least one pharmaceutically acceptable carrier or excipient is provided.

In another embodiment of the present invention, a use of the reassortant influenza virus strain in the manufacture of a live vaccine for protecting infection of influenza viruses. In a preferred embodiment, the live vaccine is a trivalent vaccine including two human influenza A subtypes and one influenza B type.

In still another embodiment of the present invention, a dual use of the reassortant influenza virus strain in early protection and long-term prolonged protection against currently circulating influenza viruses.

In a preferred embodiment, the early protection is a protecting influenza infection of host at or after about one day from vaccination. In a preferred embodiment, the long-term prolonged protection is a protection for more than a month. In a more preferred embodiment, the long-term prolonged protection is a protection up to between 6 months and one year. In another preferred embodiment, the influenza virus is a human influenza virus or an avian influenza virus. In a more preferred embodiment, the human influenza virus is a human influenza virus A or B.

In still another embodiment of the present invention, a method for early and long-term protecting against an influenza virus infection comprising administrating a pharmaceutically effective amount of the live vaccine of the present invention to a person in need of protection against the influenza virus is provided.

In still another embodiment of the present invention, a method of generating attenuated influenza strain comprising serially passing a mother strain which carries 6 internal genomes of A/PR/8/34(H1N1) and two surface antigens HA and NA of A/Aichi/2/68(H3N2) at progressively low temperature, initially at 30 and followed by 27 and 24 C is provided.

In another aspect of the present invention, a live vaccine comprising the attenuated influenza virus strain and the reassortant influenza virus strain as pharmaceutically effective ingredients and at least one pharmaceutically acceptable carrier or excipient is provided.

The PT-IV-01 based vaccine is therefore useful for prevention of seasonal influenza episodes and sudden outbreak of influenza pandemics of predicted or unknown identity.

The present inventors initially pursued developing high-yielding live influenza virus vaccine donor strain. To this end, the present inventors began to passage a high-yielding influenza strain, a reassortant between A/PR/8/34(H1N1) and A/Aichi/2/68(H3N2) (hereafter, 'mother strain'). This virus carries 6 internal genomes of A/PR/8/34(H1N1) and two surface antigens HA and NA of A/Aichi/2/68(H3N2), and is therefore essentially identical to A/PR/8/34 in internal gene structure. Capitalizing on its high-growth property, the mother strain has long been used as a 'donor strain' for annual generation of reassortant viruses that carry 6 internal genes of A/PR/8/34 backbone and HA and NA genes from the epidemic strains of particular influenza season. During the process of isolating homogeneous population of vaccine viruses and characterization of their phenotypes, the present inventors came across a novel influenza isolate (PT-IV-01) that has virtually all the desired attributes of an ideal vaccine as described above. Moreover, using PT-IV-01 strain, reassortant viruses, PT-IV-01re, could be generated that carry the HA and NA surface antigens from current virulent viruses and the 6 internal RNA genomes of A/PR/8/34 origin inherited from the cold-adapted PT-IV-01. The PT-IV-01re is as attenuated as the parental PT-IV-01 strain but immunologically identical to the virulent virus. The PT-IV-01re therefore is suitable for conferring long-term protection when given well ahead of infection by virulent viruses.

The vaccine not only provides the usual antibody-mediated protection when given sufficient time ahead of infection, but provides extremely fast protection within 1-4 days before infection even in the absence of specific antibody responses. Surprisingly, the vaccine conferred broad-spectrum protection against various subtypes of influenza viruses including human influenza A/H1N1, A/H3N2 viruses and influenza B virus and avian influenza virus as well. For this purpose, either the parental PT-IV-01 or the reassortant PT-IV-01re could be used since early protection does not depend on the nature of surface antigens. Therefore, the vaccine is ideal for pre-planned protection against the seasonal human influenza and immediate protection from sudden influenza outbreaks including avian influenza pandemics. A broad-spectrum and immediate protection provided by PT-IV-01 or the reassortant PT-IV-01re may offer a prompt measure for minimizing initial spread of virus and mitigating the impact of unexpected influenza outbreaks.

Unlike previously developed live influenza vaccine strain that provides partial therapeutic effects against sub-lethal dose of challenge, the PT-IV-01 exhibits novel effects hitherto unknown. 1) protection even against lethal challenge, 2) extremely broad protection against different subtypes including H5 type avian influenza virus, 3) broad-spectrum protection against lethal challenge of influenza A (heterologous) or B virus (heterotypic), and 4) better protection against more virulent viruses.

The novel immediate and broad spectrum protection was achieved in the absence of specific antibody response. Vaccination immediately prior to challenge resulted in the generation of significant pool of reassortant viruses between the vaccine and virulent strains suggesting that the acquisition of attenuating gene(s) from the live vaccine contributes in part to the attenuation of virulence. More importantly, the vaccination also resulted in immediate release of marker pro-inflammatory cytokines for innate immune response, such as IL-6, IL-1β and TNF-α (Nat Med 11, s23-28, 2005). The results suggest that innate immune responses play an important role in immediate protection (*Science* 300: 1524-25, 2003). It should be noted that vaccine efficacy could be increased by implementing with innate immune boosting effect (*Nat Med* 11: S63-68, 2005). Thus, genetic interference and innate immune responses play a role independently and synergistically towards early protection by live influenza vaccination. However, a poor (or rather inverse) correlation between the genetic interference and protection efficacy suggests that actually the innate immune response plays much greater role in early protection. Moreover, when given well ahead of infection (24 weeks before infection), the vaccine stimulated specific antibody response conferring extremely efficient long-term protection against virulent infection. Based on these hitherto unknown novel properties, PT-IV-01 is suitable for dual use purpose; for both immediate broad-spectrum protection against unknown influenza species of which the identity is yet to be confirmed, and long-term prolonged protection against predicted or circulating influenza subtypes.

Ideal attributes for live vaccine comprises safety, efficacy, user-friendliness and high productivity. Usually, safety of live vaccine is correlated with reduced growth and infectivity compromising the efficacy and the productivity of vaccine. To overcome this hurdle, a judicious choice of maternal strain from which vaccine strain is derived from is important. Here, the vaccine strain used for preparation of the attenuated influenza virus strain of the present invention is derived from high-yielding influenza strain (a reassortant between A/HK/6/68 and A/PR/8/34; hereafter 'mother strain'). This mother strain carries 6 internal genomes of A/PR/8/34(H1N1) and two surface antigens HA and NA of A/Aichi/2/68(H3N2). As a backbone strain for the production of killed or inactivated influenza vaccine, the mother strain has been passaged in embryonated eggs for many years, and therefore retained high-growth phenotype in eggs and host-range attenuated phenotypes (*J Infect Dis* 141, 362-365, 1980). Here the mother strain was subjected to repeated passage at low temperature (cold-adaptation) for further attenuation. This would render the vaccine strain extremely safe since the strain underwent attenuation procedure twice and attained double layer of safety, and yet the vaccine strain retains high growth phenotype as the mother strain. After extensive search from the pool of the cold-adapted virus, we came across a novel vaccine strain PT-IV-01 that provides hitherto unknown property of extremely early protection against variety of influenza strains and subtypes. PT-IV-01 could be administered in a non-invasive manner preferably through nasal route.

The novel attenuated influenza virus strain and reassortant influenza virus strain of the present invention was prepared as follows briefly:

Generation of Attenuated Influenza Virus by Repeated Passage at Low Temperature

Specific pathogen free (SPF) eggs were used for continuous passage of the mother strain for cold-adaptation. Fertilized eggs were incubated at 37° C. for 10 to 1 days for embryogenesis. The embryonated eggs were briefly incubated at desired temperatures for 3-5 hours before virus inoculation. Each group of embryonated eggs (5 eggs/group) was inoculated via allantoic route with 100 ul of virus solution containing 0.1 to 0.001 hemagglutination units (HAU). Allantoic fluids were harvested after 3 to 4 days of infection and the virus titer was estimates by hemagglutination (HA) assay. The allantoic fluid that exhibited highest virus titer was selected and used for the subsequent passage. Initial passage was conducted at 30° C. for 19 times. Then subsequent passage was followed: 40 times at 27° C. and finally 33 times at 24° C.

Isolation of PT-IV-01 Strain

Madin-Darby canine kidney (MDCK) cells were grown in minimal essential medium (MEM) supplemented with 10% fetal bovine serum (FBS). The cells were cultured as monolayers in the MEM medium supplemented with 10% heat-inactivated fetal bovine serum. The cells were used for plaque purification of the virus that underwent final passage at 24° C. Confluent MDCK cells were washed with serum free MEM media and incubated at room temperature with ten fold dilutions in MEM of allantoic fluid of 24° C. passaged eggs. The inoculum was then removed, and the cells were overlaid with medium containing 10 μg/ml trypsin and 1% low-melting agarose and incubated at 37° C. in 5% $CO_2$ incubator. Individual plaques were isolated, and repeated plaque assay was performed to ensure the genetic homogeneity of the isolate. Each plaque was then amplified in embryonated eggs and examined for various characters and parameters indicative of safety, efficacy and productivity. One independent isolate that carried all desirable characters was named as PT-IV-01 and deposited on Apr. 24, 2007 at KCCM (Korea Culture Center of Microorganisms) located in 4361-221, Yurim B/D, Hongje-1-dong, Seodaemun-gu, SEOUL 120-091, Republic of Korea under Accession NO: KCCM 10854P in compliance with the Budapest Treaty on the International Recognition of the Deposit of Microorganisms for the Purpose of Patent Procedure. The depositor of the microorganism assures that (a) all restrictions on the availability to the public of the deposited material referred to in paragraph 2 will be irrevocably removed upon issuance of a United States patent of which any of such deposited material is the subject; (b) the deposited material will be maintained for a period of at least five years after the most recent request for the furnishing of a sample of any of the deposited material was received by the KCTC and, in any case, for a period of at least 30 years after the date of deposit or for the effective life of such patent, whichever is longer; (c) should any of the deposits become non-viable or mutated, or otherwise incapable of being famished by the depository upon request due to the condition of the deposit, it will be replaced by Applicants; and (d) access to the cultures will be available to the Commissioner during the pendency of the patent application or to one determined by the Commissioner to be entitled to such cultures under 37 C.F.R. §1.14 and 35 U.S.C. §122.

The RNAs were isolated from the virus, and using the segment specific primers, RT-PCR was performed and the sequence was verified for six internal RNA genomes (PB2, PB1, PA, NP, M, NS, respectively) as provided in the sequence listing (SEQ ID NOs: 1-6).

Characterization of ts, ca, att Phenotypes of PT-IV-01

The temperature sensitive (ts), cold-adapted (ca) and attenuated (att) phenotypes of PT-IV-01 were evaluated in vitro, in ovo and in vivo. The growth characteristics of PT-IV-01 were evaluated at different temperature in ovo as follows. Embryonated eggs were inoculated with 0.1 HAU of PT-IV-01 or reassortants thereof (PT-IV-01re) and incubated at 25° C., 30° C. and 37° C. Allantoic fluids were harvested 3 days after inoculation and the yield of infectious virus was assayed at 30° C. in MDCK cells. Likewise, the growth in vitro was evaluated by infection and culture in MDCK cells at different temperatures.

The attenuation phenotype of PT-IV-01 was evaluated by nasal administration of mice. For each exponent, a group of eight mice were immunized intranasally with the vaccine strain. Six-week-old female BALB/c mice were housed in filter-isolate cages. The mice were inoculated 5 days after arrival. Prior to inoculation (day 0), the mice were anesthetized with ketamine (0.4 mg/mice). Fifty microliters of virus inoculum were delivered intra-nasally by 200 ul pipet tip to the anesthetized mice. The body weight and any clinical signs were monitored daily.

Generation and Identification of Reassortant Viruses

Reassortant virus was generated by the following procedure. 11-day-old embryonated eggs were co-infected with the cold-adapted PT-IV-01 and wild-type virus at a same titer and incubated at 30° C. After 3 days incubation, allantoic fluids were harvested. To select 6:2 reassortant virus from these random reassortant mixture, viruses were passaged in the presence of antiserum against PT-IV-01 at 25° C. in MDCK or primary chicken kidney (PCK) cells. The viruses were selected by plaque assay in the presence of anti PT-IV-01 antiserum at 25° C. Here, the successful selection of desired reaasortant viruses among two different viruses usually depends on the quality of the antiserum against the donor virus.

The antiserum for PT-IV-01 virus was generated by the following procedure. The virus PT-IV-01 were cultured in eggs and purified by ultracentifugation. Viruses are adsorbed to adjuvant such as $Al(OH)_3$ and are injected into guinea pigs and rabbits via subcutaneous route. After one month, the serum was taken from the immunized animals, separated by centrifugation and inactivated by treating at high temperature. And then the serum is treated with kaolin to reduce the non-specific reaction between RBC (red blood cells) and serum. The serum is then cleared of small debris by passing through 0.22 um filter, and it is then stored in small aliquot at −70° C. until use. The reassortant viruses that carry surface antigens of virulent origin would not be neutralized by the antiserum and therefore survive the treatment and make plaques in this process.

The plaque purification can be done using the MDCK cells or primary chicken kidney (PCK) cells. The PCK cells were obtained by the following procedure. The 18~19-day-old embryonated hen's eggs were sanitized with 70% ethanol and opened by scissors. Embryo was withdrawn from the egg, and the legs were removed to help isolation of kidneys located near backbone. The kidneys were washed with PBS, and then the connective or fat tissues attached to the kidney were removed carefully. The kidneys were washed again with PBS and transferred to a small beaker. The kidneys were chopped by scissors and washed with PBS, and then pre-heated PBS and trypsin (usually 2.5% (w/v)) were added. After incubation with gentle stirring, the cell suspension was passed through gauge filter on the funnel/flask containing FBS. The cells were then transferred to a new tube and washed with growth medium. After the propagation of the cells in T-flasks, the cells were harvested and preserved at liquid nitrogen gas tank until use.

Isolated plaques from PCK or MDCK cells were then amplified in embryonated chicken eggs. The ca and is phenotype of plaque purified viruses were determined according to their plaquing efficiency at different temperatures in the range of 25° C. to 40° C. in MDCK or PCK cells. Finally, the identities of their genetic components were analyzed by RT-PCR dependent genome analysis method.

For characterization of the reassortant viruses, it is very important to finally identify and confirm the origin of eight RNA genomes. For this purpose, the RNA genes could be reverse transcribed into cDNA by RT-PCR (reverse transcription—polymerase chain reaction) and the sequence of the cDNA can be determined. Generally, RNAs isolated from virus is initially reverse transcribed with universal primer. And then, selective RNA segment could be further amplified by the segment-specific primers. For this purpose, segment specific primers could be designed for selective amplification of particular RNA genome. If the size of the amplified DNAs derived from various RNA segments is sufficiently different, then the specific primer sets can be combined and more than two different RNAs can be amplified in a multiplex manner. After final identification of desired 6:2 RNA ratio, then the nucleotide sequences of genome segments for HA and NA are finally determined. This is a final check for the genetic stability of HA and NA during reassortment process. Since there always is a possibility of nucleotide change in the RNA genome due to high mutation rate intrinsic to influenza virus, the comparison of the sequences between before and after reassortment process as a final check is important.

Immunization, Broad-Spectrum Immediate Prophylaxis and Long-Term Protection

The prophylactic effect of vaccine could be evaluated by experimental infection of susceptible animals (5-6 week old BALB/c mice, for example). To ensure statistical significance for the results, eight animals per experimental group are used. For immediate protection, mice were vaccinated daily by intranasal route with varying dose of PT-IV-01 or reassortant virus (PT-IV-01re) thereof, up to four days prior to challenge. Mice were usually anesthetized before receiving lethal dose of virulent virus, such as A/New Caledonia/99 or B/Shangdong/97. In parallel, therapeutic effect of the vaccine virus can also be evaluated by coinfection of mice with virulent virus in time of vaccination. Here, the dose of both virulent and the vaccine viruses could be varied to evaluate the optimal condition for prophylaxis or therapeutic effect. In general, varying titers ($1.0\times10^3$ to $1.0\times10^6$ PFU) of vaccine dose are used before lethal challenge with about 5-10 $LD_{50}$ of virulent viruses. Alternatively, vaccination was also performed according to standard procedures: a month interval between vaccination and challenge. All mouse studies were performed under the regulation of the Animal Care Committee at Yonsei University.

Antibodies, Proinflammatory Cytokines and Genetic Interference During Vaccination and Challenge.

After vaccination of animals, the level of antibodies can be determined by enzyme-linked immunosorbent assay (ELISA). Therefore, in a certain time interval, each group of mice were sacrificed by cervical dislocation and bronchoalveolar lavage (BAL) fluid was for the titration of IgA and cytokine levels. IgG titration was performed using serum obtained from the same mice (twelve animals per experimental group). For the titration of IgG and IgA antibodies, a microwell plate coated with antigen, preferably the challenge virus A/NC/99 or B/SD/97, are usually used.

Induction of the antiviral innate immune response is mediated by host pattern-recognition receptors including Toll-like receptor (TLR), which provides first hand protection from various viral infection (*Nat Immunol* 7, 131-137, 2006). During this process, TLR family members sense various pathogens through pattern recognition receptors to activate common signaling pathways (*J Pediatr* 144, 421-429, 2004). To evaluate whether the vaccination elicit innate immune response, the marker cytokines for innate immune response, such as IL-6, TNF-α and IL-1β are monitored after vaccination. Alternatively, type 1 antiviral responses are monitored by measuring IFN-α.

Administration of the live vaccine disclosed above to an individual can be by any known or standard technique. These include oral ingestion, gastric intubation, or broncho-nasal-ocular spraying. All of these methods allow the live vaccine to easily reach the NALT, GALT or BALT cells and induce antibody formation and cell mediated immunity and are the preferred methods of administration. Other methods of administration, such as intravenous injection, that allow the carrier microbe to reach the individual's blood stream can be acceptable. Intravenous, intranasal, intramuscular or intramammary injection is also acceptable with other embodiments of the invention, as is described later.

The immunization dosages required will vary with the antigenicity of the live vaccine product and need only be an amount sufficient to induce an immune response. Routine experimentation will easily establish the required amount. Multiple dosages are used as needed to provide the desired level of protection.

The pharmaceutical acceptable carrier or excipient in which the live vaccine is suspended or dissolved may be any solvent or solid or encapsulating material such as for a lypholized form of the vaccine. The carrier is non-toxic to the inoculated individual and compatible with the microorganism or antigenic gene product. Suitable pharmaceutical carriers are known in the art and, for example, include liquid carriers, such as normal saline and other non-toxic salts at or near physiological concentrations, and solid carriers, such as talc or sucrose. Gelatin capsules can serve as carriers for lypholized vaccines. Adjuvants may be added to enhance the antigenicity if desired. When used for administering via the bronchial tubes, the vaccine is preferably presented in the form of an aerosol. Suitable pharmaceutical carriers and adjuvants and the preparation of dosage forms are described in, for example, Remington's Pharmaceutical Sciences, 17th Edition, (Gennaro, Ed., Mack Publishing Co., Easton, Pa., 1985).

The present invention will be described in more detail with examples. The following examples are only for demonstration of the present invention, but does not limit the range of the claims of the present invention.

EXAMPLE 1

Cold-Adaptation of Influenza a Virus

The mother strain was subjected to repeated passage in embryonated chicken eggs at progressively lower temperatures to select virus with mutations that would produce a cold-adapted and temperature-sensitive phenotypes. Eggs were incubated at 30° C., 27° C. or 24° C. for 3-5 hours before virus inoculation and then incubated at the same temperature after inoculation. For each temperature, 5 or 6 embryonated eggs were injected via allantoic route. The inoculum (100 μl) contained 0.001 HAU to 0.1 HAU. Infected allantoic fluids were harvested after 72 or 96 hours and titrated by HA assay. Among these, the highest growth virus were selected and used for the next passage. Following the procedure, the mother strain was serially passaged 19 times in embryonated chicken eggs at 30° C. and then serially passaged additional 40 times at 27° C. Finally, this virus was further passaged 33 times in embryonated chicken eggs at 24° C. This cold-adapted virus was plaque purified three times and amplified at 24° C. to make working stocks. An isolate was named PT-IV-01, and has been deposited at Korea Culture Center of Microorganisms, Korea, on Apr. 24, 2007 under Accession number: KCCM 10854P.

EXAMPLE 2

Growth Characterization of PT-IV-01 Cold-Adapted Influenza Virus in Embryonated Chicken Eggs The growth characteristics of PT-IV-01 was examined and compared with the mother strain in embryonated chicken eggs. Embryonated eggs were inoculated with 0.1 RAU of PT-IV-01 or the mother strain and incubated at 37° C., 30° C. and 25° C. Allantoic fluid was harvested 3 days after inoculation and titrated with HA assay. As shown in Table 1, PT-IV-01 virus grew in eggs at 25° C., whereby the mother strain was not detected in HA assay. When growth pattern of the PT-IV-01 and the mother strain were compared at 37° C., the yield of the PT-IV-01 virus was significantly lower than the mother strain. As a result, the cold-passaged PT-IV-01 virus exhibited both cold-adapted phenotype and restricted growth phenotype at body temperature in embryonated chicken eggs. Overall, the growth profile is shifted in favor of low temperature thanks to repeated passage at low temperature. Notably, the virus titer of the PT-IV-01 was comparable to that of the mother strain, suggesting that even after extensive attenuation procedure, high growth phenotype is still maintained.

TABLE 1

| | Virus titer (log2 HAU) | | |
|---|---|---|---|
| strain | 25° C. | 30° C. | 37° C. |
| PT-IV-01 | 7 ± 0.5 | 11 ± 1 | 6 ± 1 |
| Mother strain | — | 11 ± 1 | 11 ± 1 |

EXAMPLE 3

Growth Characterization of PT-IV-01 Cold-Adapted Influenza Virus in Animal Cell Line The ca and ts properties of the PT-IV-01 virus were assessed by plaque assay on MDCK cell at both low and high temperatures. Plaque forming unit (PFU) were compared at three different temperatures, 25° C., 33° C. and 39° C. The plates of infected virus were incubated 5-7 days at 25° C. and 2-3 days at 33° C. and 39° C. Growth at 33° C. was used as the standard condition.

As shown in Table 2, the PT-IV-01 virus formed plaques efficiently at 25° C., but inefficiently at 39° C. The result showed that PT-W-01 virus had appropriate cold-adapted and temperature-sensitive properties in animal cell lines, extending similar observations in embryonated eggs. Clearly, the optimal temperature for plaque formation was shifted in favor of low temperature. It is worth noting that the virus titer of PT-IV-01 (8.1-8.6 log 10 pfu/ml) is similar to that of the mother strain (8.4-8.5 log 10 pfu/ml), suggesting that high growth phenotype is still maintained. The results suggest that MDCK certified cell lines could be used as substrates for the production of PT-IV-01 influenza vaccine in good yields.

TABLE 2

| | Virus titer (log10 pfu/ml) | | |
|---|---|---|---|
| Strain | 25° C. | 33° C. | 39° C. |
| PT-IV-01 | 8.1 | 8.6 | 2.8 |
| Mother strain | 2.1 | 8.5 | 8.4 |

EXAMPLE 4

Characterization of PT-IV-01 Cold-Adapted Influenza Virus in Mice

Six-week-old female BALB/c mice were used as a laboratory model to assess potential virulence of the PT-IV-01 virus. BALB/c mice were infected intranasally with 50 μl of the virus at different dilutions. After inoculation with varying dose of PT-IV-01 or the mother strain ($10^5$-$10^7$ PFU/mouse), clinical signs and weight loss of mice were constantly monitored from day 0 to 16 post-infection.

Figure 1B:
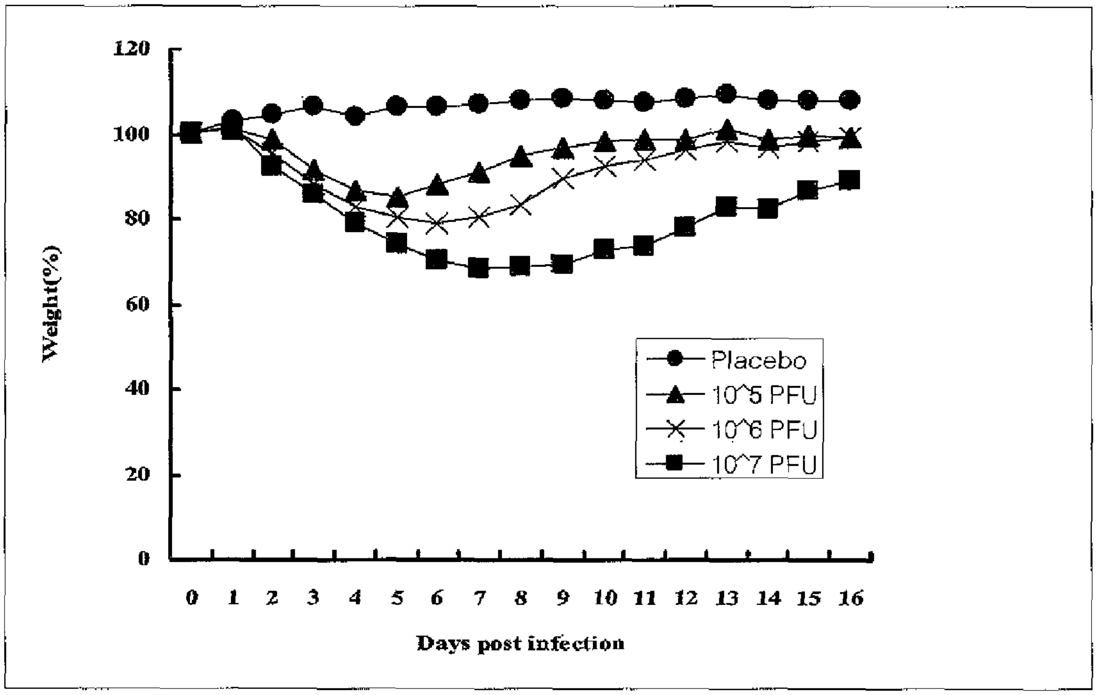
FIG. 1B is a graph showing effects of viral inoculation with mother strain virus on weight-loss in BALB/c mice. Same symbols are used as FIG. 1A for each experimental group.
Figure 1C:
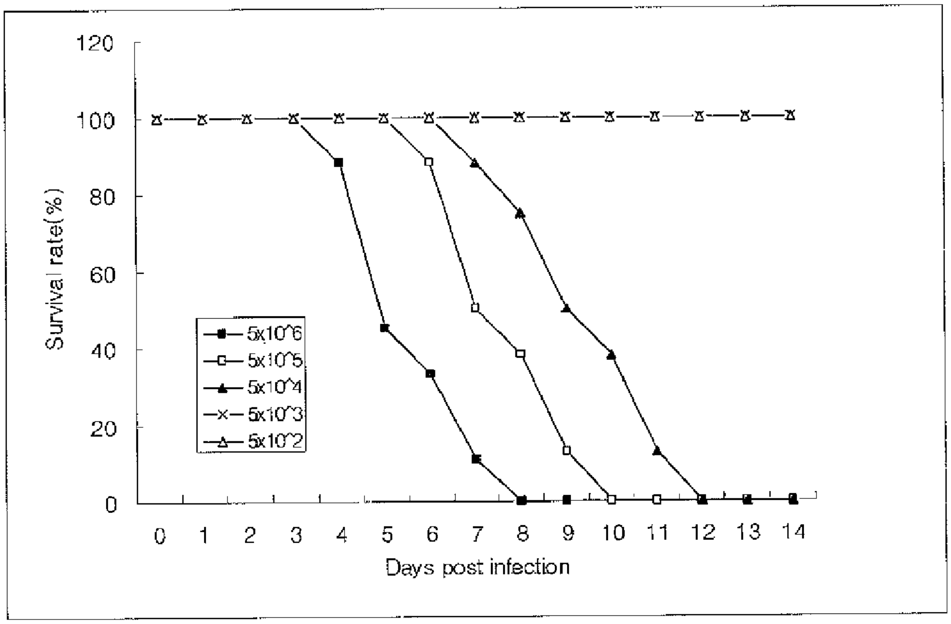
FIG. 1C is a graph showing effects of viral inoculation with A/PR/8/34 virus on survival rate in BALB/c mice. The A/PR/8/34 virus was inoculated at different titers ($10^2$-$10^6$ PFU/mouse) and the monitored daily. Inoculated with $10^2$ PFU/mouse (Δ), inoculated with $10^3$ PFU/mouse (x), inoculated with $10^4$ PFU/mouse (▲), inoculated with $10^5$ PFU/mouse (□) and inoculated with $10^6$ PFU/mouse (■).

As shown in FIG. 1, Mice infected with cold-passaged PT-IV-01 virus significantly reduced severity of clinical signs associated with influenza virus infection (FIG. 1A). The mother strain infected group showed significant clinical signs as compared to the placebo control or PT-IV-01 virus inoculated groups (FIG. 1B). Clinical signs and weight loss was most prominent at 4 to 6 days post-infection although no mortality was observed with the mother strain. In contrast, the group of mice receiving PT-IV-01 virus did not show any clinical sign even at highest titer tested. These results suggested that the PT-IV-01 virus is highly attenuated. As a control, the virulence of A/PR/8/34 virus was also examined (FIG. 1C). All mice succumbed after $5\times10^4$ pfu dose of infection. It should be noted that the mother strain used for the generation of PT-IV-01 was reassortant carrying six internal genes derived from A/PR/8/34 strain. And yet, no mortality was observed for the mother strain even at the highest titer tested although partial virulence (as scored by weight loss) was significant. This result suggests that, as compared to the original A/PR/8/34 virus (FIG. 1C), the mother strain was already partially attenuated (FIG. 1B) even before cold-adaptation, and PT-IV-01 was further attenuated by cold-adaptation (FIG. 1A). Therefore, the highly attenuated phenotype of PT-IV-01 was ascribed to double layer of attenuation, initially by repeated passage of mother strain in embryonated eggs (host-range phenotype) followed by further passage at low temperature (cold-adapted phenotype).

EXAMPLE 5

Sequence Analysis of the PT-IV-01 Virus Genome

The entire genome of the cold-passaged PT-IV-01 virus was analyzed. The full genome segments of PT-IV-01 were amplified by RT-PCR, and then the PCR products were excised from agarose gel and used as templates for sequencing. The primers and reaction composition for transcription and amplification are listed in Table 3-1 and 3-2.

TABLE 3-1

| | Primer sets | |
|---|---|---|
| | Sense (SEQ ID NOs) | Anti-sense (SEQ ID NOs) |
| PB2 | agcgaaagcaggtcaattata (SEQ ID NO: 7) | agtagaaacaaggtcgtt (SEQ ID NO: 8) |
| PB1 | agcgaaagcaggcaaaccat (SEQ ID NO: 9) | agtagaaacaaggcattt (SEQ ID NO: 10) |
| PA | agcgaaagcaggtactgat (SEQ ID NO: 11) | agtagaaacaaggtactt (SEQ ID NO: 12) |
| NP | agcaaaagcagggta (SEQ ID NO: 13) | agtagaaacaagggtatt (SEQ ID NO: 14) |
| M | agcgaaagcaggtagat (SEQ ID NO: 15) | agtagaaacaaggtagtt (SEQ ID NO: 16) |
| NS | agcaaaagcagggtgacaaa (SEQ ID NO: 17) | agtagaaacaagggtgtt (SEQ ID NO: 18) |

TABLE 3-2

| Composition of PCR tube | |
|---|---|
| Components | Volume (final concentration) |
| 10 × PCR Buffer (GIBCO-BRL) | 5 μl (1 X) |
| 50 nM Magnesium Sulfate | 2 μl (2 mM) |
| 10 nM dNTPs | 1 μl (0.2 mM) |
| 10 pmol/μl sense primer | 2 μl (0.4 pmol/μl) |
| 10 pmol/μl anti-sense primer | 2 μl (0.4 pmol/μl) |
| Template(RT product) | 1 μl/3 μl (PA only) |
| Platinum Taq polymerase (GIBCO-BRL, 5unit/μl) or ExTaq (Takara, 5unit/μl) | 0.2 μl (1 unit) |
| Double distilled water | 36.8 μl/34.8 μl (PA only) |
| Total volume | 50 μl |

The RT reaction mixture was incubated at 37° C. for 60 min to induce cDNA synthesis, and then reaction tube was incubated at 94° C. for 5 min to inactivate reverse transcriptase. PCR was then proceeded as follows: initial denaturation at 94° C. for 2 min, followed by 40 cycles of 94° C. for 30 sec, 40-45° C. for 30 sec, and 68° C. for 2 min 30 sec. A final incubation was performed at 68° C. for 5 min. At least four different internal primers were used for sequence analysis of each segment of PT-IV-01. When necessary, additional sequencing was performed for both DNA strands to confirm the sequence. The whole sequence of the six internal RNA genomes (PB1, PB2, PA, NP, M and NS) are shown in Sequence Listing (SEQ ID NOs: 1 to 6).

EXAMPLE 6

Generation and Characterization of Reassortant Virus

Live attenuated influenza vaccines are prepared by annual reassortment of the attenuated donor strain and contemporary epidemic strains. The segmented nature of the RNA genome of influenza viruses allows reassortment of RNA segment to occur in doubly infected cells. Therefore, attenuated reassortant virus can be produced by mating an attenuated influenza virus strain PT-IV-01, which serves as a donor of attenuating genes, with a wild-type influenza virus. The resulting live attenuated reassortant virus PT-IV-01re inherits the two RNA segments encoding hemagglutinin (HA) and neuraminidase (NA) surface glycoproteins from the contemporary epidemic virus and the six internal RNA segment from PT-IV-01.

The present invention generates reassortant influenza virus between PT-IV-01 and A/New Caledonia/20/99(H1N1) viruses. PT-IV-01 virus was mixed with the virulent wild-type A/New Caledonia/20/99(H1N1) virus in a predetermined ratio and inoculated into 11-day-old embryonated specific pathogen free (SPF) chicken eggs. After one day, the allantoic fluid was harvested and inoculated into new eggs in the presence of antibodies specific to PT-IV-01, and then the eggs were incubated at low temperature to select only viruses carrying the cold-adaptation property of the donor virus as well as outer envelop proteins HA and NA from the wild type virus. Virus clones obtained by plaque isolation on primary chicken embryo kidney (PCEK) or Mardin-Darby canine kidney (MDCK) cells in the presence of the same antibodies were grown again in fertilized eggs for further propagation. The reassortant virus clones were screened initially by hemagglutination inhibition and neuraminidase inhibition assay, and then their genetic composition was analyzed by multiplex RT-PCR. The final clone was named as PT-IV-01re (A/NC). Similarly, reassortant virus between PT-IV-01 and A/Panama/2007/99 (H3N2) was generated and the final clone was named as PT-IV-01re(A/PA).

The growth properties of the reassortant virus were measured at various temperatures in MDCK cells. As shown in Table 4, reassortant virus showed both cold-adapted and temperature-sensitive phenotype as expected from the parental PT-IV-01.

TABLE 4

| | Virus titer(log10 pfu/ml) | | |
|---|---|---|---|
| Strain | 25° C. | 33° C. | 39° C. |
| PT-IV-01re (A/NC) | 6 | 6.4 | <2.8 |
| PT-IV-01re (A/PA) | 5.2 | 5.9 | <2.8 |

EXAMPLE 7

Analysis of Immunogenicity and Protective Efficacy of PT-IV-01re (A/NC)

The reassortant virus ($1\times10^8$ PFU per ml allantoic fluid), was obtained by inoculation with SPF(specific pathogen free) chicken eggs and incubation for three days at the temperature of 30° C. Likewise, wild type virus A/New Caledonia/20/99 (H1N1) ($3\times10^7$ PFU per ml allantoic fluid), was obtained by inoculation of SPF eggs and incubation at 37 C for three days.

Figure 2A:
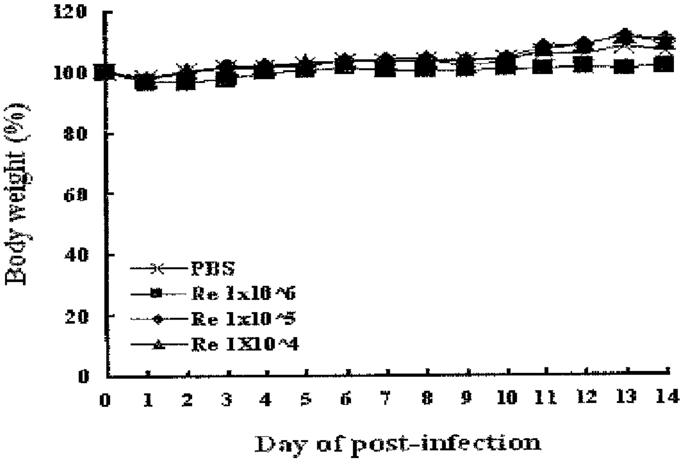
FIG. 2A is a graph showing body weight changes of BALB/c mice after intranasal infection with reassortant virus. Negative control (X), inoculated with $1\times10^6$ PRU (■); inoculated with $1\times10^5$ PFU (♦) and inoculated with $1\times10^4$ PFU (▲).
Figure 2B:
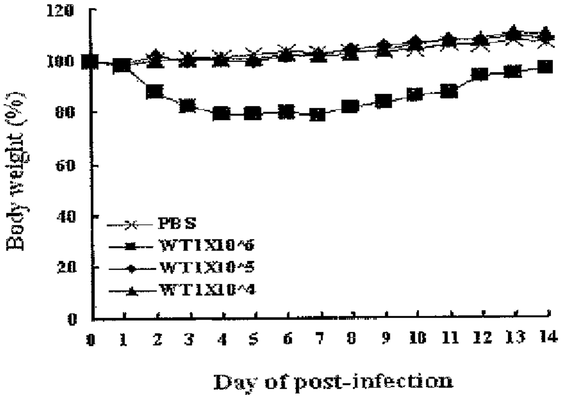
FIG. 2B is a graph showing body weight changes after intranasal infection with wild-type A/New Caledonia/20/99 (H1N1) viruses. Same symbols are used as FIG. 2A for each experimental group.
Figure 2C:
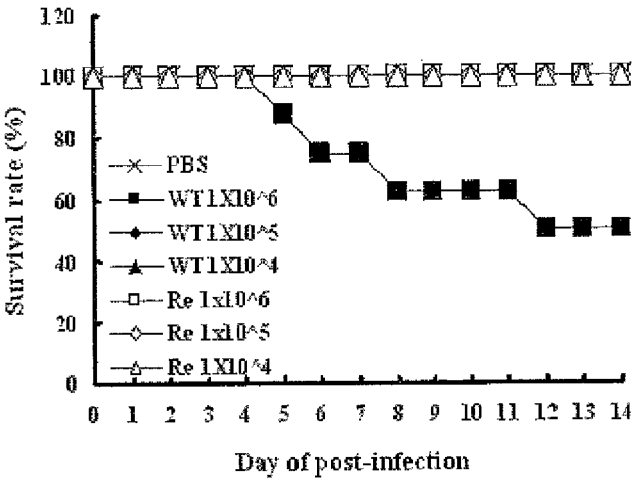
FIG. 2C is a graph showing effects of viral inoculation with A/New Caledonia/20/99 (H1N1) reassortant viruses and wild-type viruses on survival rate in BALB/c mice. PBS control (X), inoculated with $1\times10^6$ PFU of wild-type virus (■), inoculated with $1\times10^5$ PFU of wildtype virus (♦) and inoculated with $1\times10^4$ PFU of wild-type virus (▲), inoculated with $1\times10^6$ PFU of reassortant virus (□), inoculated with $1\times10^5$ PFU of reassortant virus (◇) and inoculated with $1\times10^4$ PFU of reassortant virus (Δ).

BALB/c mice received either reassortant virus (PT-IV-01re) (A/NC) or wild type virus A/New Caledonia/20/99 (H1N1) at indicated titer ($1\times10^6$, $1\times10^5$ and $1\times10^4$ PFU/mouse). PBS (phosphate buffered saline) control was included for comparison. The mortality and morbidity (in terms of weight loss) were monitored daily after challenge. As shown in FIG. 2, the PT-IV-01re(A/NC) retained attenuated phenotype consistent with highly attenuated phenotype observed with the parental PT-IV-01 virus.

Mice were bled from retro-obital venous plexus 19-day after vaccination with reassortant viruses and induced antibody titers were determined by HI assay. As shown in Table 5, virus specific serum antibodies were detected in the sera of mice inoculated with all dose and these antibody titers were increased depending on inoculation titer.

TABLE 5

| Groups | HI titer |
|---|---|
| PBS | <32 |
| A/NC (H1N1) reassortant ($1 \times 10^6$) | 1184 ± 352 |
| A/NC (H1N1) reassortant ($1 \times 10^5$) | 380 ± 139.25 |
| A/NC (H1N1) reassortant ($1 \times 10^4$) | 312 ± 104 |

Figure 3A:
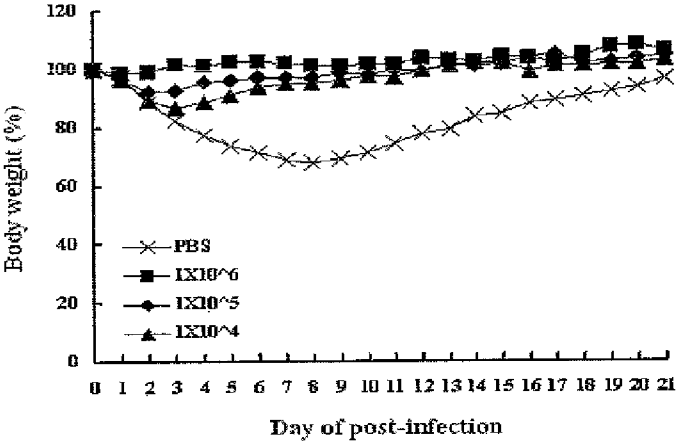
FIG. 3A is a graph showing body weight changes of six-week-old female BALB/c mice after challenge infection with A/New Caledonia/20/99 (H1N1) wild-type virus. PBS negative control (X), vaccinated with $1\times10^6$ PFU of reassortant virus (■), vaccinated with $1\times10^5$ PFU of reassortant virus (♦) and vaccinated with $1\times10^4$ PFU of reassortant virus (▲).
Figure 3B:
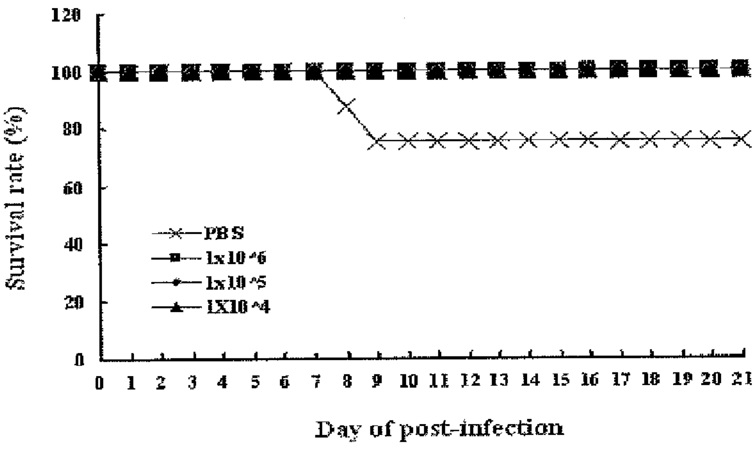
FIG. 3B is a graph showing survival rates after challenge infection with wild-type A/New Caledonia/20/99 (H1N1). Same symbols are used as FIG. 3A for each experimental group.

Three weeks after vaccination, mice were challenged with A/New Caledonia/20/99(H1N1) wild type virus (1 $LD_{50}$). As shown in FIG. 3, all groups of mice vaccinated with reassortant virus did not show notable clinical signs or weight loss and survived the challenge infection of wild-type virus. In contrast, wild type infection led to notable weight loss and 50% mortality at high dose of infection ($1\times10^6$ pfu). The results show that the PT-IV-01re vaccine provides efficient protection against infection by virulent viruses.

EXAMPLE 8

Extremely Early Protection from Heterologous Challenge

Figure 4A:
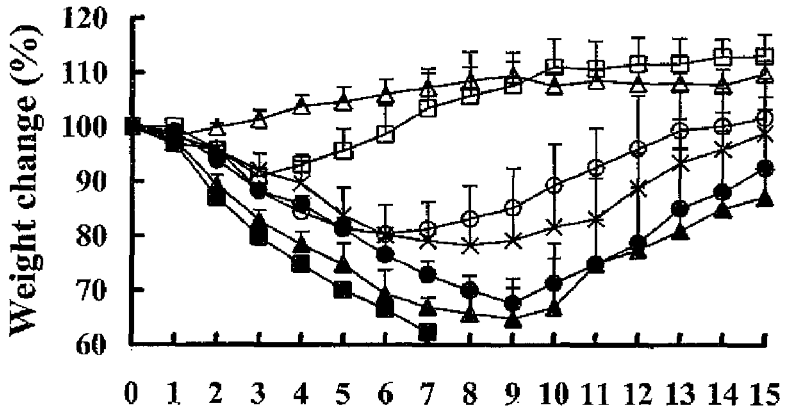
FIG. 4A is a graph showing body weight changes of BALB/c mice after challenge with lethal dose of A/New Caledonia/20/99 virus. PBS control (A), −4d group (□), −3d group (○), −2d group (x), −1d group (●), mix group (▲), without vaccination (■). The dose for vaccination was $1.0\times10^6$ PFU/mouse and the challenge with $2LD_{50}$ ($5.0\times10^5$ PFU/mouse). Data are shown as means±SEM (n=8).
Figure 4B:
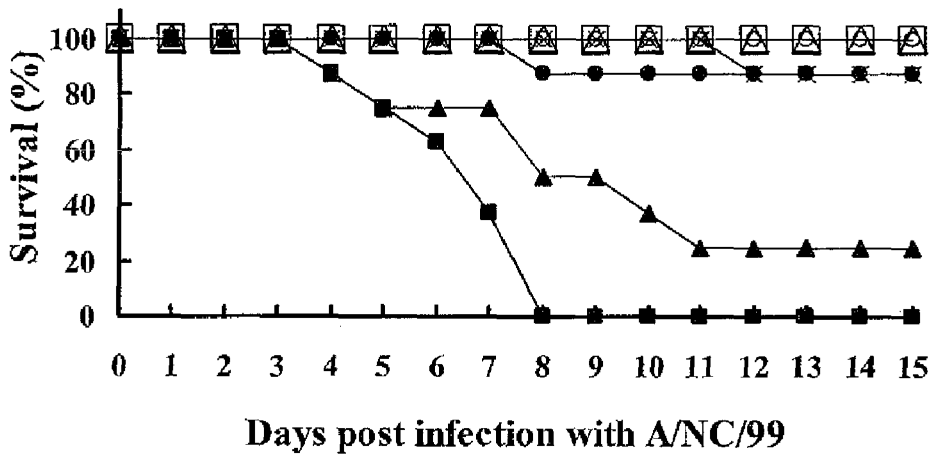
FIG. 4B is a graph showing survival rate of mice in FIG. 4A after challenge with A/New Caledonia/20/99. Same symbols are used as FIG. 4A for each experimental group.

To evaluate prophylactic property of PT-IV-01 virus (H3N2), mice were vaccinated prior to virulent virus challenge A group of 5 to 6-week-old BALB/c mice received $1.0\times10^6$ PFU of PT-IV-01 virus by intranasal route at one day intervals up to four days before lethal infection with A/New Caledona/20/99 (A/NC/99, H1N1). One group of mice were vaccinated and challenged simultaneously (mixed infection) to test potential interference of vaccine virus on virulence. Different from traditional vaccine approach, our strategy arms protection against various strains of influenza. Thus we selected A/NC/99 (H3N2) for challenge virus rather than same subtype (H1N1) influenza A virus. The interference was determined by daily examination on body weight (FIG. 4A) and survival (FIG. 4B).

Prior vaccination with the PT-IV-01 virus 1-4 days before challenge resulted in dramatic reduction of weight loss and mortality associated with influenza infection. The mortality was greatly reduced in groups vaccinated at least 1 day before challenge. Survival was 87.5% for vaccination groups of −1 and −2 day whereas 100% survival was achieved for the −3 and −4 day groups. Even in mixed infection, 25% mice survived while all mouse succumbed in non-vaccinated group.

Figure 5A:
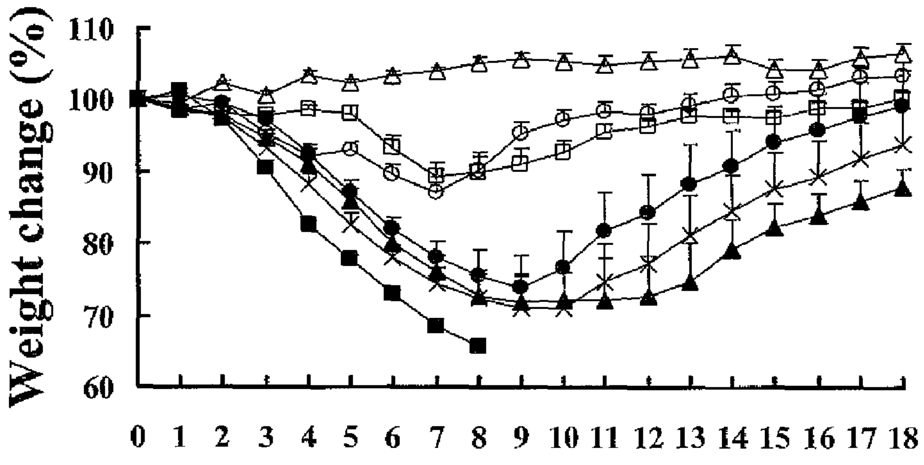
FIG. 5A is a graph showing body weight changes of BALB/c mice after heterotypic protection provided by vaccination with PT-IV-01. Vaccination and challenge schedules are identical to experiment in FIG. 4A, except B/Shangdong/7/97 virus were used as challenge virus. PBS control (A), −4d group (□), −3d group (○), −2d group (x), −1d group (●), mix group (A), without vaccination (■). The dose for vaccination was $10\times10^6$ PFU/mouse and the challenge with $2LD_{50}$ ($3.0\times10^5$ PFU/mouse). Data are shown as means±SEM (n=8).

The protection was most outstanding for vaccines 4 days before challenge (−4d group). The morbidity was greatly reduced as compared to other groups and the body weight regained only after 3 days post challenge. Mice that were vaccinated 3 days before challenge (−3d group) also resulted in 100% survival but clinical symptoms were more pronounced than the −4d group. The difference suggests a certain time intervals between vaccination and challenge are required for efficient protection. The group of mice that was vaccinated only 1 day before challenge (−1d group) showed notable clinical symptoms resulting in about 30% of body weight loss. And yet, compared to non-vaccinated group (NC only group), the morbidity and mortality were greatly reduced. Even when mice were simultaneously infected with PT-IV-01 and A/NC/99 (mix group), marked reduction in virulence was observed. The fact that even a mixed infection reduced toxic effect of A/NC/99, where the total virus titer that was introduced into mouse were 3-fold higher than A/NC/99 only group, strongly suggests interference of virulence by vaccine virus. Considering morbidity and mortality, it is concluded that protection is better in the order of −4d>−3d>−2d>−1d>0d (mixed infection). Overall result of heterologous protection is similar to heterotypic protection (example 10 and FIG. 5). In general, better protection is provided with increased intervals between vaccination and challenge. Moreover, the effect of genetic interference between vaccine and virulent virus peaks at −2d and continues to decrease on −3d and −4d (example 14 and Table 7). This means that better protection from heterologous challenge on −3d or −4d group than −2d group is not due to genetic interference but rather to innate immune response elicited by PT-IV-01 (example 13 and FIG. 9).

EXAMPLE 9

Determination of Vaccine Dose for Early Protection

Vaccination induces adaptive immune response comprising antigen specific antibody responses and cell-mediated immune response that provides efficient protection. As is the case with adaptive immune response, innate immune response and genetic interference could also be influenced by the vaccine dose. However different dose strategy may be used to induce early protection against various subtypes. To test this, we vaccinated mice with $1.0\times10^3$, $1.0\times10^4$, $1.0\times10^5$ and $1.0\times10^6$ PFU of PT-IV-01 at one day before challenge with heterologous H1N1 virus ($5.0\times10^5$ PFU).

Administration of mice with PT-TV-01 even at highest dose ($1.0\times10^7$ PFU) failed to show any clinical symptoms due to highly attenuated phenotype. We, therefore, set maximum vaccine dose to $1.0\times10^6$ PFU that is 10 fold lower than virus titer that could be used in our experimental setting without notable clinical signs. Mice vaccinated in. $1.0\times10^3$ PFU at 1 day before challenge was 100% lethal showing that $1.0\times10^3$ PFU is insufficient titer to induce early protection. Another groups of mice were vaccinated with $1.0\times10^4$, $1.0\times10^5$, $1.0\times10^6$ PFU and survived 25, 50, 87.5% respectively Liable 6). From these results, we conclude higher vaccine dose are required for better protection by vaccination at 1 day before challenge.

TABLE 6

Survival rate of mice vaccinated at different doses

| Group | Survival |
|---|---|
| No challenge | 8/8 (100%) |
| $1.0 \times 10^6$ PFU | 7/8 (87.5%) |
| $1.0 \times 10^5$ PFU | 4/8 (50%) |
| $1.0 \times 10^4$ PFU | 2/8 (25%) |
| $1.0 \times 10^3$ PFU | 0/8 (0%) |
| No vaccination | 0/10 (0%) |

EXAMPLE 10

Extremely Early Protection from Heterotypic Challenge

The live vaccine was also evaluated for protection against lethal influenza B virus challenge. Experimental schedule is essentially same as shown in example 8 but different challenge virus B/Shangdong/7/97 was used. Lethal dose of B/Shangdong/7/97 is $1.5\times10^5$ PFU and 2 $LD_{50}$ ($1.5\times10^5$ PFU) of virus were used for challenge mice.

Figure 5B:
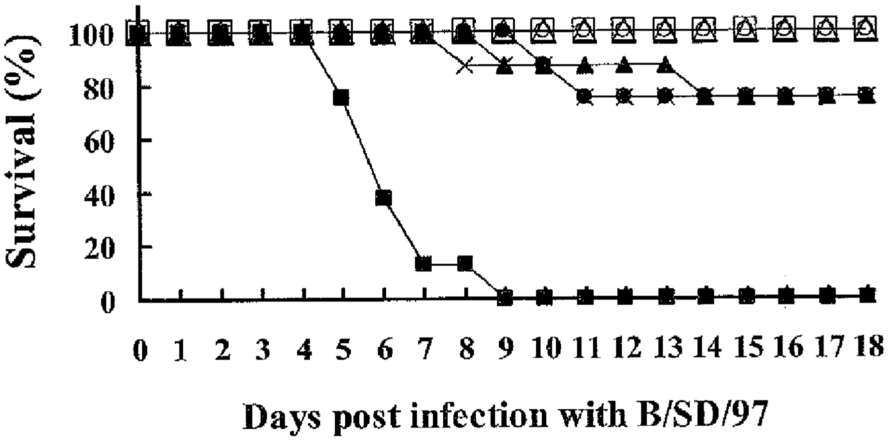
FIG. 5B is a graph showing survival rate of mice in FIG. 5A after challenge with B/Shangdong/7/97. Same symbols are used as FIG. 5A for each experimental group.

Similar pattern of body weight loss were observed as in heterologous interference (FIG. 5A). 100% survival and reduced morbidity was shown in mouse vaccinated −3 and −4 days before B/SD/97 challenge, while 75% survival was shown for the −1, −2 day and mix groups (FIG. 5B).

Reassortants between influenza A and B viruses are not observed in nature nor readily generated in laboratory (J Virol 77, 8031-8038, 2003), and therefore, the heterotypic protection conferred by influenza A vaccine from lethal challenge by the influenza B virus is due to the innate immune response rather than to genetic interference between the vaccine (PT-IV-01) and the challenge virus (see example 14 and Table 7). Consistent with this interpretation is that there is a degree of specificity between influenza A and B strains in their recognition of promoters (J Viol 70, 1232-1236, 1996). The results further extend protection from heterologous challenge (example 8, FIG. 4) that innate immune response plays a greater role than genetic interference for early protection.

EXAMPLE 11

Extremely Early Protection from Avian Influenza Infection

Figure 6:
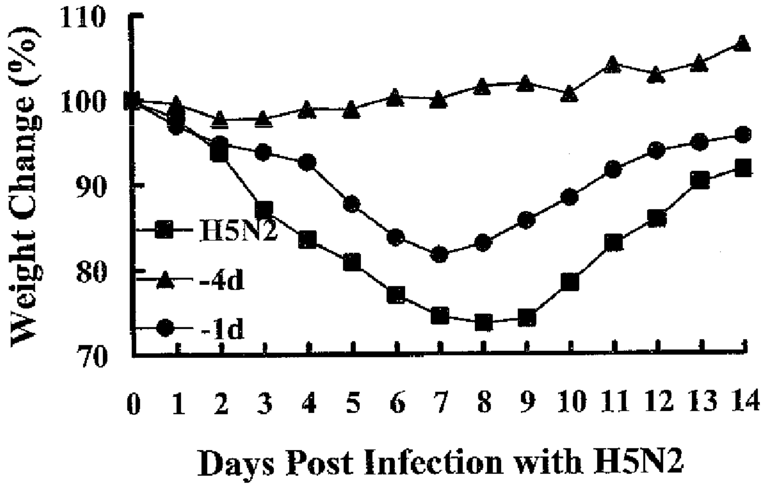
FIG. 6 is a graph showing body weight changes of BALB/c mice after vaccination with $1.0\times10^6$ PFU of PT-IV-01 virus 1 (●) or 4 (▲) days before challenge. Mice were examined for early protection form avian influenza (H5N2) infection. Body weight was checked for 2 weeks. Results are compared to control group without vaccination (■).

From the results described previously, we can expect immediate and broad-spectrum protection against various influenza strains by administration of donor virus. We further examined the early protection from H5 subtype avian influenza virus which is closely related to potential pandemic candidate. The experiment proceeded as explained in example 8. We vaccinated mice with PT-IV-01 at 1 and 4 days before challenge (FIG. 6).

Vaccination with PT-IV-01 1 day or 4 day prior challenge with A/Aquatic Bird/Korea/W81/06 (H5N2) significantly reduced clinical symptoms associated with virulent infection. Mice vaccinated at 4 days before challenge exhibited more efficient protection than the groups immunized 1 day before.

EXAMPLE 12

Early Protection is Provided without Specific Antibody Responses

Generally, vaccination with influenza vaccine stimulates adapted immune responses and generates antigen specific antibody production. These antibodies are key mediator in clearance of followed virus infection. However, the fact that early interference exhibited similar protection to various strains may suggest neutralizing acquired immune responses are not heavily involved. To prove this possibility, we examined antibody responses at early time points after vaccination in mice.

Figure 7A:
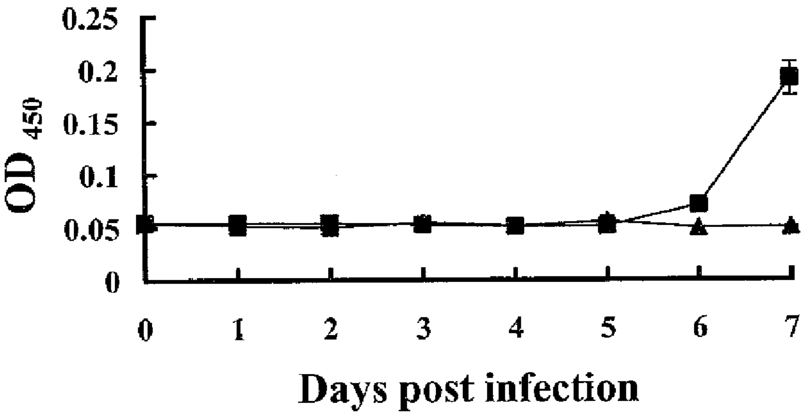
FIG. 7A is a graph showing result of ELISA analysis for PT-IV-01 specific IgA in BAL fluid after vaccination with PT-IV-01. Mice were vaccinated ($1.0\times10^6$ PFU/mouse) to examine production of PT-IV-01 specific antibodies in vaccinated mice. PBS controlled (▲) and vaccinated (■) mice were analyzed daily for production of PT-IV-01 specific IgA in BAL fluid. Significant antibody level was detected 6 days post infection.

PT-IV-01 virus specific IgA antibody in BAL fluid (FIG. 7A) and IgG antibody in serum (FIG. 7B) of vaccinated or PBS controlled mice were tested for their specificity to virus by enzyme-linked immunosorbent assay (ELISA).

Figure 7B:
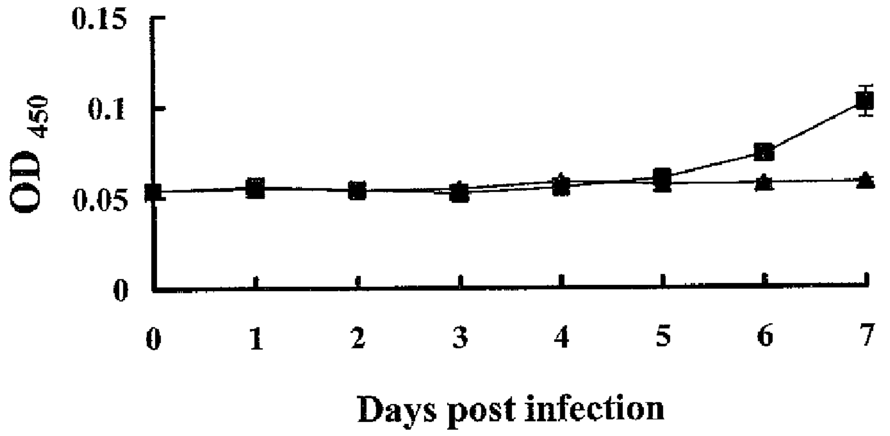
FIG. 7B is a graph showing results of ELISA analysis for PT-IV-01 specific IgG in BAL fluid after vaccination with PT-IV-01. Serum samples were taken from the same mice as in FIG. 7A to examine PT-IV-01 specific IgG antibody production. Significant antibody level was detected 5 days post infection.

A microwell plate was coated with $5.0\times10^5$ PFU of PT-IV-01 virus in PBS buffer (pH 7.4). After washing with 50 mM Tris-HCl containing 0.05% Tween-20, plate was blocked with PBS containing 1% BSA for 1 hour at room temperature. BAL fluid and serum samples were added to each well and incubated for 1 hour at room temperature. After washing, HRP conjugated anti-mouse IgG/IgA monoclonal antibody was added and incubated for 1 hour. After washing, tetramethylbenzidine (TMB) solution was added, incubated for 30 minutes at room temperature and stop solution ($2NH_2SO_4$) was added. The absorbance was measured at 450 nm on ELISA reader. Antibody titers were checked for 7 days and elevation of IgA and IgG level was observed at least 5 days post vaccination. As evident in FIG. 7, there was no detectable production of virus specific antibody until 5 days post vaccination either in IgA in BAL fluid (FIG. 7A) or in IgG in serum (FIG. 7B).

Influenza B virus infection was effectively prevented by vaccination with influenza A vaccine strain PT-IV-01 (example 10). We therefore tested if PT-IV-01 specific antibody can interact with influenza B virus. We used ELISA as described earlier using microwells coated with either A/New Caledonia/20/99 or B/Shangdong/7/97 (FIG. 8).

Figure 8:
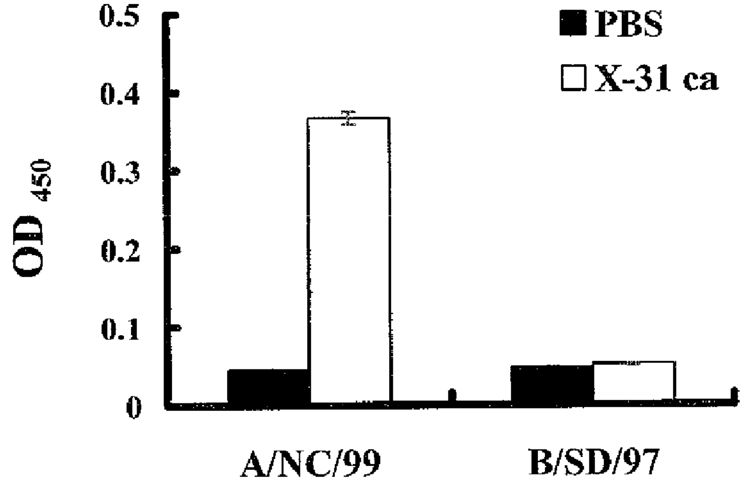
FIG. 8 is a graph showing cross-reactivity of serum IgG from mock (■) or PT-IV-01 (□) infected mice to A/NC/99, and B/SD/97. Serums from PT-IV-01 vaccinated mice showed cross-reactivity to other heterologous influenza A virus (A/NC/99) but did not recognized heterotypic B/SD/97 virus. Data are shown as means±SEM (n=8).

PT-IV-01 virus specific IgG antibodies interacted with A/NC/99, whereas cross-reactivity with B/SD/97 was hardly observed (FIG. 8). Furthermore, novel protection of PT-IV-01 against influenza B virus without antibody cross-reactivity (example 10, FIG. 5) strongly implies the involvement of broad-spectrum innate immune response.

EXAMPLE 13

Analysis of Pro-Inflammatory Cytokines Stimulated by PT-IV-01

Innate immune response provides first line of defense from viral infection. Different from acquired immune response which induces selective protection, innate immune response provides resistance to various pathogens in a short period. We examined whether innate immune response by vaccination with donor virus contributes to early interference.

Figure 9A:
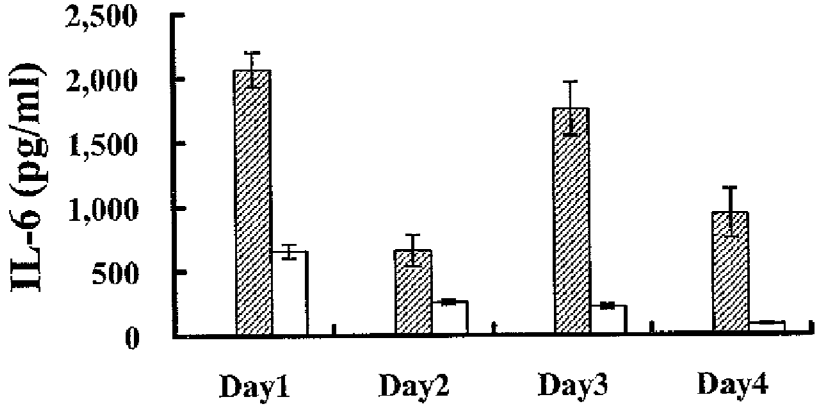
FIG. 9 are graphs showing production of pro-inflammatory cytokines after vaccination with PT-IV-01 induces production of pro-inflammatory cytokines. The mean concentration of IL-6, TNF-α and IL-1β in BAL fluid were determined from mouse infected with mock (■), mother strain (▩, $1.0\times10^6$ PRU), and PT-TV-01 (□, $1.0\times10^6$ PFU). Data are shown as means±SEM and represents three independent experiments (n=12). ND; not detected.
Figure 9B:
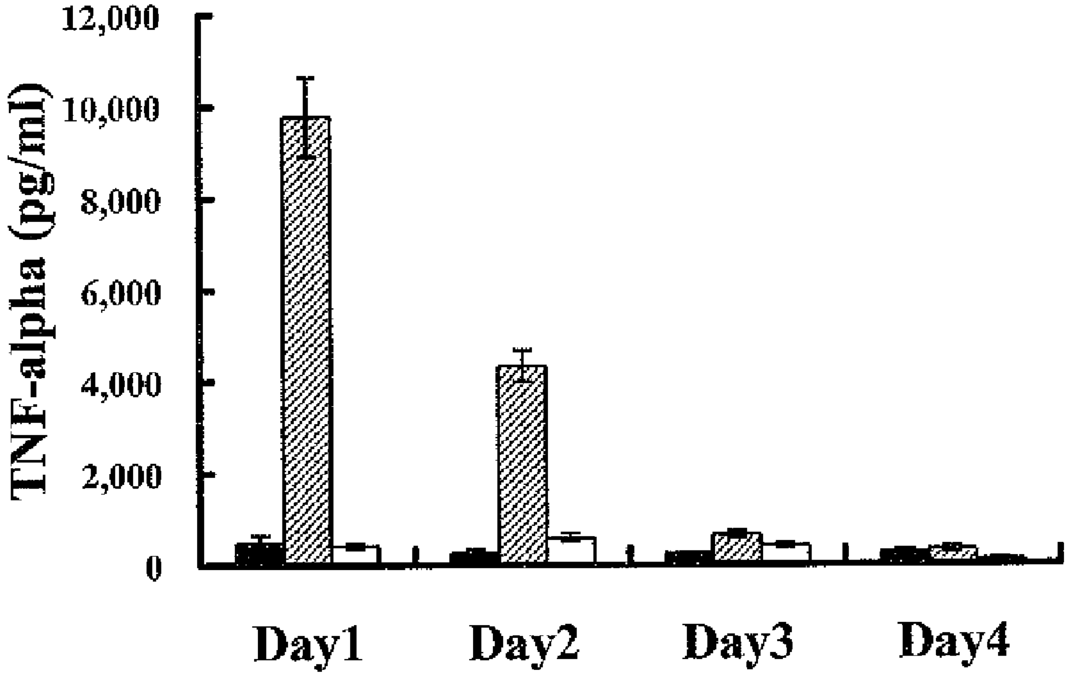
Figure 9C:
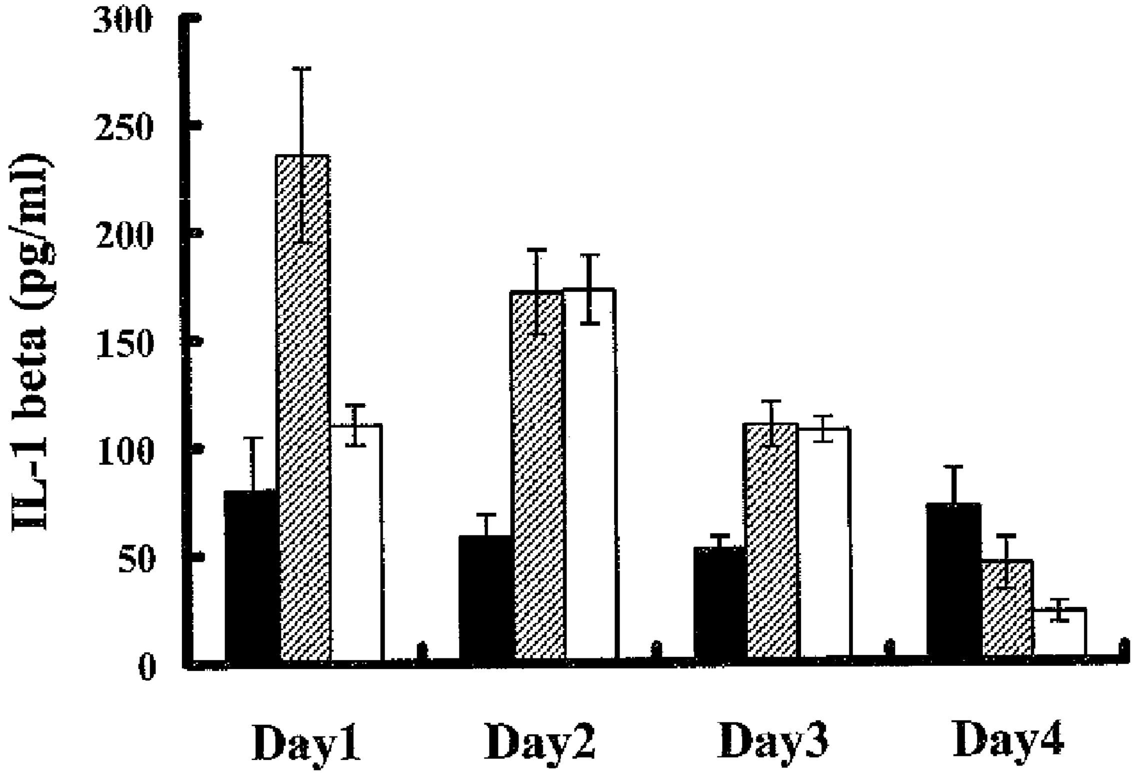

We used IL-6, TNF-alpha, IL-1 beta for marker cytokines for innate immune response. Specific antibodies against these pro-inflammatory cytokines are used in ELISA to analyze cytokine level of BAL fluid samples obtained from mice vaccinated with PT-IV-01 virus. Groups of mice were vaccinated with $1.0\times10^6$ PFU of donor virus and BAL fluid were prepared for 4 days. In comparison, the cytokine level was also monitored from mice infected with the same titer ($1.0\times10^6$ PFU) of the mother strain before cold-adaptation (FIG. 9).

PT-IV-01 virus infection stimulated lower, but distinct level of pro-inflammatory cytokines when compared to the mother strain infection. These results may reflect attenuated phenotype of PT-IV-01 virus. The decrease of pro-inflammatory cytokines was most pronounced on the level of TNF-$\alpha$ among all cytokines monitored in our experiment. And yet, the level of IL-6 and IL-1$\beta$ is still maintained. IL-1$\beta$ was stimulated at a low level in both the mother strain and PT-IV-01 infected mice. From these results, we conclude that vaccination with the cold-adapted PT-IV-01 stimulates milder but distinct innate immunity than strong and acute inflammation frequently associated with virulent infection.

EXAMPLE 14

Genetic Interference Plays a Minor Role in Early Protection

In a mixed infection of A/NC/99 and PT-IV-01, the survival rate was markedly improved as compared with A/NC/99 only infection (FIGS. 1 and 2). Under this condition, the innate immune response is not expected to play significant role on protection. We therefore considered possibility of interference in gene level.

The PT-IV-01 virus used in the present study has accumulated 16 nucleotide substitutions in all 6 internal genomes during subsequent passage at low temperature, which collectively contributes to attenuated phenotypes.

To estimate direct interference among influenza RNAs, several groups of mice were vaccinated and challenged at various time intervals as in example 8. After 24 hours post challenge, viruses were isolated from infected mice, plaque purified, and the RNA composition was analyzed by the multiplex RT-PCR method. For the detection of PT-IV-01 derived RNAs, we used 8 pairs of PT-IV-01 specific primers, which has previously been confirmed for their specificity.

50 independent plaques were isolated from lung homogenate of the infected mice for each group and total 250 different plaque isolates were analyzed (table 7). We observed significant population of reassortants (10-30%) among different groups of varying intervals of vaccination and challenge, where the reassortant population was highest (46%) in the mixed infection. Generation of reassortant shows that multiple infections occurred in the epithelial cells of mouse respiratory tract and suggests the possibility of competition between the two viral species in gene level.

Example 10 (and FIG. 5) showed that protection is better in the order of −4d>−3d>−2d>−1d>0d (mixed infection). Table 7 actually shows that the genetic interference between vaccine and virulent virus actually decreases on −3d and −4d group. The results shows that the genetic interference plays minor role, if at all, to early protection whereas broad-spectrum innate immune response plays a major role.

TABLE 7

Ratio of reassortant virus generated by vaccine strain PT-IV-01 and the virulent A/NC/99

| | | Viruses analyzed by multiplex RT-PCR | | | Ratio of |
|---|---|---|---|---|---|
| Group | n[a] | PT-IV-01 | A/NC/99 | Reassortant | reassortant |
| −4d | 50 | 0 | 45 | 5 | 10% |
| −3d | 50 | 4 | 36 | 10 | 20% |
| −2d | 50 | 27 | 8 | 15 | 30% |
| −1d | 50 | 11 | 33 | 6 | 23% |
| mix | 50 | 6 | 21 | 23 | 46% |
| Total | 250 | 48 | 143 | 59 | 24% |

[a]Number of tested plaques

EXAMPLE 15

Analysis of Immunogenicity of PT-IV-01 Based Reassortant Vaccine

Mice were anaesthetized with pentobarbital sodium (55 mg/kg/0.2 ml) by intra-peritoneal (i.p.) route, and vaccinated with 50 ul of the PT-IV-01re(A/NC) or PT-IV-01re(A/PA) by intranasal (i.n.) route. Negative control mice were infected with the same volume of buffer used for vaccine formulation. The mice were sacrificed 4 weeks later, and the sera, nasal wash (mucosal fluid) and BAL (Bronchoalveolar lavage, lung airway) fluid were collected and analyzed by HI and EIA. To collect BAL fluid, a 1-mL syringe (26G needle) containing 1 mL of PBS was inserted into the trachea to the lung direction and tightened with a string to prevent the leakage of solution. Pumping of the PBS was repeated 3 times. Collected fluid was transferred to a new tube containing 10 ul of 100× protease inhibitor cocktail (PIC, 100 μM Pepstatin A, 1 mM Leupeptin, 20 mM Pefabloc SC (AEBSF)). The solution was centrifuged at 10,000 rpm for 5 mm, and then 0.5 mL of the supernatant was transferred to a new tube containing 5 μL of 10×PIC and 50 μL of PBS (0.10% BSA). BAL fluid was stored at −20° C. until use.

After the collection of BAL fluid, the under jaw of the mouse was removed, and a 1-mL syringe containing 1 mL of PBS (0.1% BSA) was inserted into naso-pharynx. While clipping with forceps prevented the back-flow, nose was washed. Collected fluid, nasal wash was transferred to a new tube containing 10 μL of 100× protease inhibitor cocktail (PIC, 100 μM Pepstatin A, 1 mM Leupeptin, 20 M Pefabloc SC (AEBSF)). The solution was centrifuged at 10,000 rpm for 5 min, and then 0.5 mL of the supernatant was transferred to a new tube containing 5 μL of 10×PIC and 50 μL of PBS (0.1% BSA). Nasal wash was stored at −20° C. until use.

The amount of antibody was assayed by HI and EIA. The HI titer was taken as the highest dilution factor that gave inhibition of hemagglutination against eight HA units of virus, and the titer of EIA was the highest dilution factor which gave absorbance above 0.2. EIA titers were calculated according to the method of Reed and Muench (Vaccine 21, 940-945, 2003).

EXAMPLE 16

Determination of $MID_{50}$ (Fifty Percent Mouse Infectious Dose)

Balb/c mice (5-week-old female of 16~20 g, Biogenomics co., Korea) were used to determine $MID_{50}$ titer of wt viruses. The animals were fed in isolated room (20~26° C., 40~60% humidity, 150~300 Lux, 12 h illumination) until use. Allantoic fluid containing virus was 10-fold serially diluted with NAF/SPG (Normal allantoic fluid/SPG).

Mice were anaesthetized with pentobarbital sodium (55 mg/kg/0.2 ml) by intraperitoneal (i.p.) route, and infected with 50 μL of the diluted virus solution by intranasal (i.n.) route. Control mice were infected with the same volume of NAF/SPG. The mice were sacrificed 3 weeks later, and their sera were collected and analyzed by HI. Since the protective level of HI is 40, the blood samples showing HI higher than 40 were considered as positive sera. $MID_{50}$ titers were calculated according to the method of Reed and Muench.

EXAMPLE 17

Protective Efficacy of PT-IV-01re(A/NC) Against Virulent Challenge

Four weeks after immunization with PT-IV-01 reassortant vaccine, mice were anaesthetized with pentobarbital sodium (55 mg/kg/0.2 ml) by intraperitoneal (i.p.) route, and challenged with 50 ul containing 100 $MID_{50}$ (Fifty percent mouse infectious dose) of virus by i.n. route. Control mice received the same volume of NAF/SPG. The mice were sacrificed 4 days later, and their lungs and nasal wash were collected. The lungs were homogenized in 1 ml of cold PBS including antibiotics to prevent microbial growth and the homogenates were frozen at −70° C. and later thawed and pelleted by centrifugation. Virus content was analyzed by plaque assay and real-time PCR.

Figure 10:
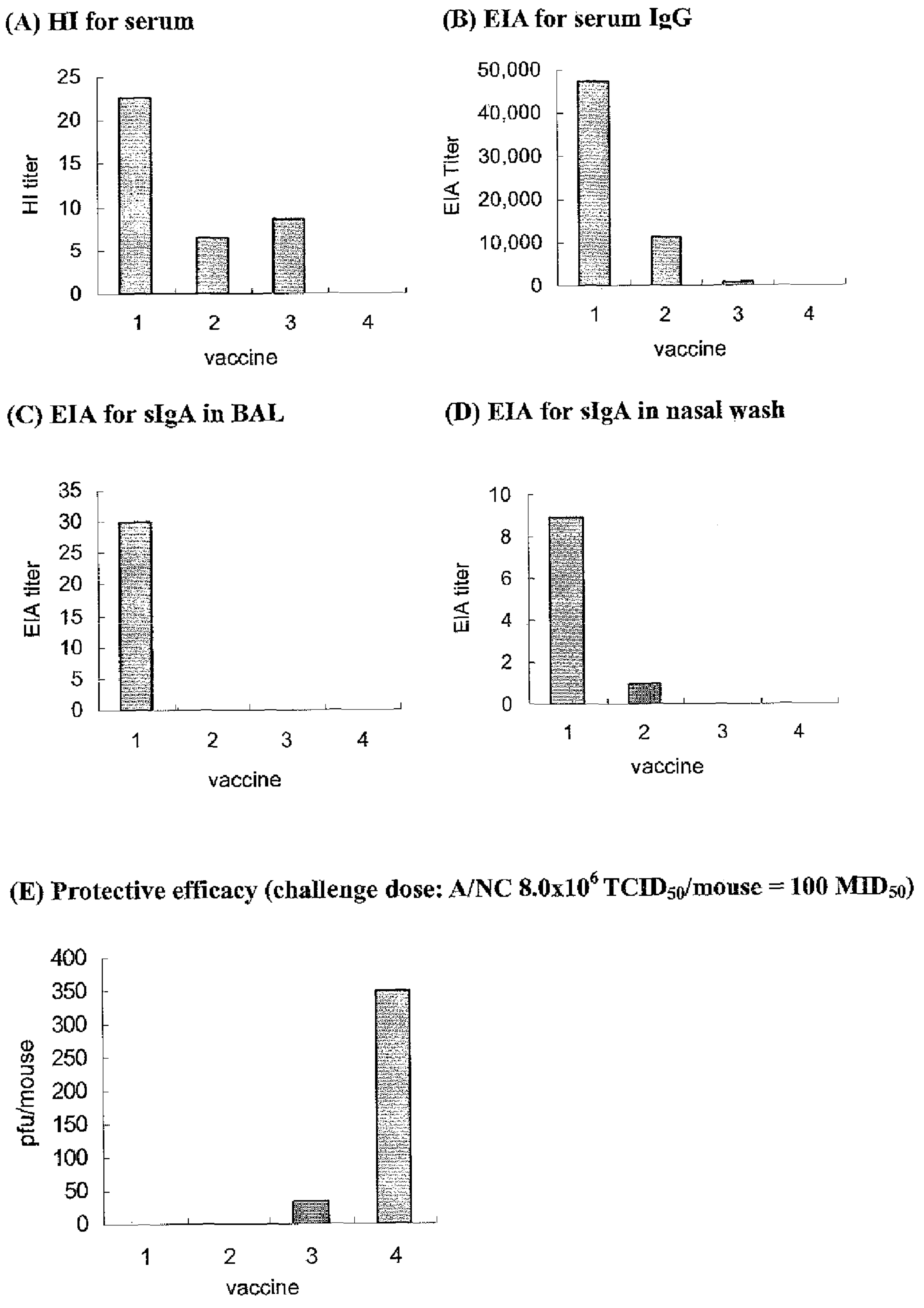
FIG. 10 are graphs showing immunogenicity and protective efficacy of PT-IV-01re(A/NC). PT-IV-01re(A/NC) and mock were given by intranasal route, and the inactivated vaccine was injected by subcutaneous route. Hemagglutination inhibition (HI) for serum (a), enzymeimmuno assay (EIA) for serum IgG (b), EIA for slgA in BAL (c), EIA for slgA in nasal wash (d) and protective efficacy of vaccines (e) were performed. 1, PT-IV-01re(A/NC). ($8.9\times10^4$ PFU); 2, PT-IV-01re(A/NC) ($8.9\times10^2$ PFU); 3, 3×0.75 ug of HA of inactivated trivalent (A/NC, A/PA, B/SD) split vaccine; 4, Mock.

The data are summarized in FIG. 10. Vaccination with PT-IV-01re(A/NC) induced IgG effectively whereas 0.75 ug HA of inactivated vaccine per mouse did not induce enough level of IgG. And secretory IgA (sIgA) was detected in BAL and nasal wash of mouse vaccinated with PT-IV-01re(A/NC) but not with inactivated vaccine. The vaccine dose of $8.9\times10^2$ PFU per mouse (group 2) was enough to completely clear the virulent A/NC/20/99 from the lung of infected mouse even without high level of antibodies. HI titer of sera from mice vaccinated with inactivated vaccine (group 3) was higher than the titer of group 2, and yet failed to clear viruses completely. This means that sIgA induced by PT-IV-01re(A/NC) neutralize challenge viruses and protect mice more effectively. The data demonstrate that PT-IV-01 based reassortant vaccine confers much better protection as compare to conventional inactivated vaccine.

EXAMPLE 18

Protective Efficacy of PT-IV-01re(A/PA) Against Virulent Challenge

Four weeks after immunization with PT-IV-01re(A/PA), mice were anaesthetized with pentobarbital sodium by intraperitoneal (i.p.) route, and challenged with 50 ul containing 100 $MID_{50}$ (Fifty percent mouse infectious dose) of A/Panama/2007/99 by i.n. route. Control mice received the same volume of NAF/SPG. The mice were sacrificed 4 days later, and their lungs and nasal wash were collected. The lungs were homogenized in 1 ml of cold PBS including antibiotics to prevent microbial growth and the homogenates were frozen at −70° C. and later thawed and pelleted by centrifugation. Virus content was analyzed by plaque assay and real-time PCR.

Figure 11:
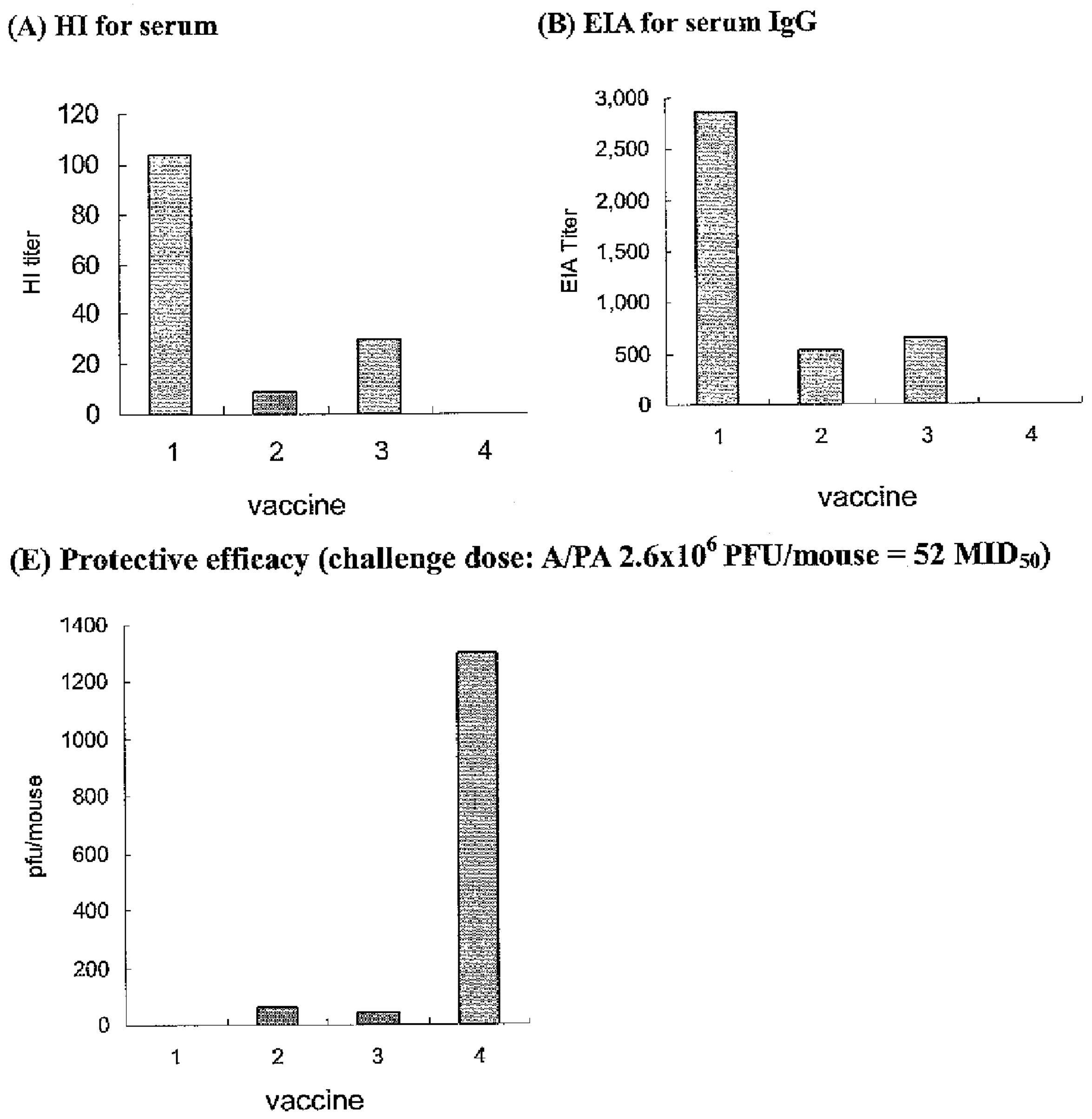
FIG. 11 are graphs showing immunogenicity and protective efficacy of PT-IV-01re(A/PA). Reassortant viruses and mock were given by intranasal route, but inactivated vaccine was injected by subcutaneous route. Hemagglutination inhibition (HI) for serum (a), enzymeimmuno assay (EIA) for serum IgG (b) and protective efficacy of vaccines (c) were performed. 1, PT-IV-01re(A/PA). ($1.9\times10^5$ PFU); 2, PT-IV-01re(A/PA) ($1.9\times10^3$ PFU); 3, 3×0.75 ug of HA of inactivated trivalent (A/NC, A/PA, B/SD) split vaccine; 4, Mock. (challenge dose of A/Panama/2007/99: $2.6\times10^6$ PFU/mouse=52 $MID_{50}$)
Figure 12:
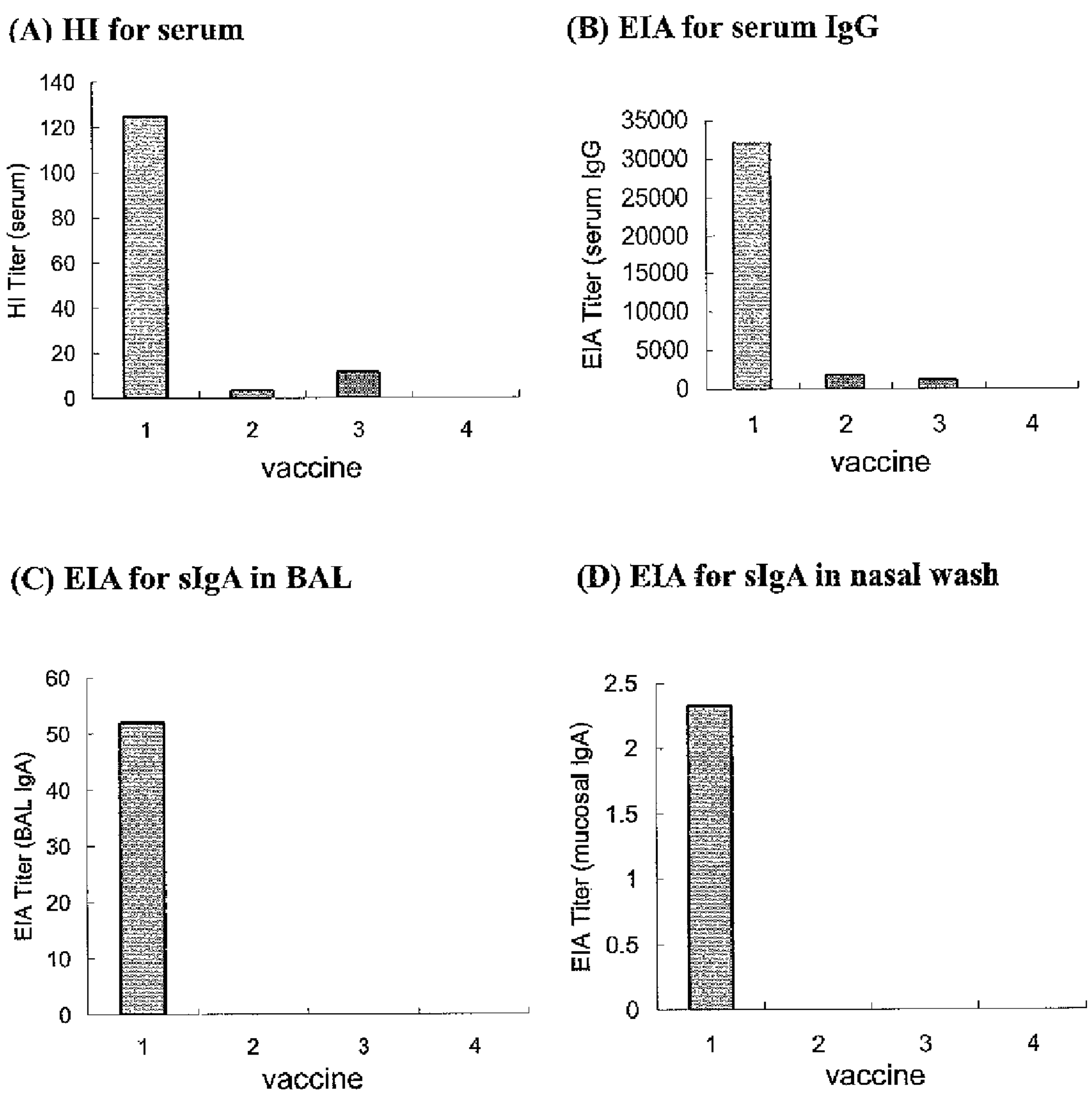
FIG. 12 are graphs showing immunogenicity of PT-IV-01re(A/PA). Mice were vaccinated by intranasal route, and the inactivated vaccine was injected by subcutaneous route. Hemagglutination inhibition (HI) for serum (a), enzymeimmuno assay (EIA) for serum IgG (b), EIA for slgA in BAL (c) and protective efficacy of vaccines (d) were performed. 1, $1\times10^{5.5}$ $TCID_{50}$ of PA-76-16; 2, $1\times TCID_{50}$ of PA-76-16; 3, 3×7.5 ug of HA of inactivated trivalent (A/NC, A/PA, B/SD) split vaccine; 4, Mock.

As shown in FIG. 11, vaccination with PT-IV-01re(A/PA) induced IgG effectively and cleared the infecting virus form the lung completely. The secretion of sIgA depends on experimental conditions, and sIgA was evident with vaccination dose of $1\times10^{5.5}$ $TCID_{50}$. The vaccine dose of $1.9\times10^5$ PFU per mouse (group 1) was enough to completely clear the virulent A/PA/2007/99 from the lung of infected mouse. Even hundred-fold lower dose of vaccination ($1.9\times10^3$ PFU) was enough to lower the infectious virulent virus by 20 fold as compared to without vaccination (Group 4). The data again demonstrate that PT-IV-01 based reassortant vaccine confers an extreme good protection from lethal challenge. The results were confirmed in a separate and independent set of experiment (FIG. 12).

EXAMPLE 19

Figure 13:
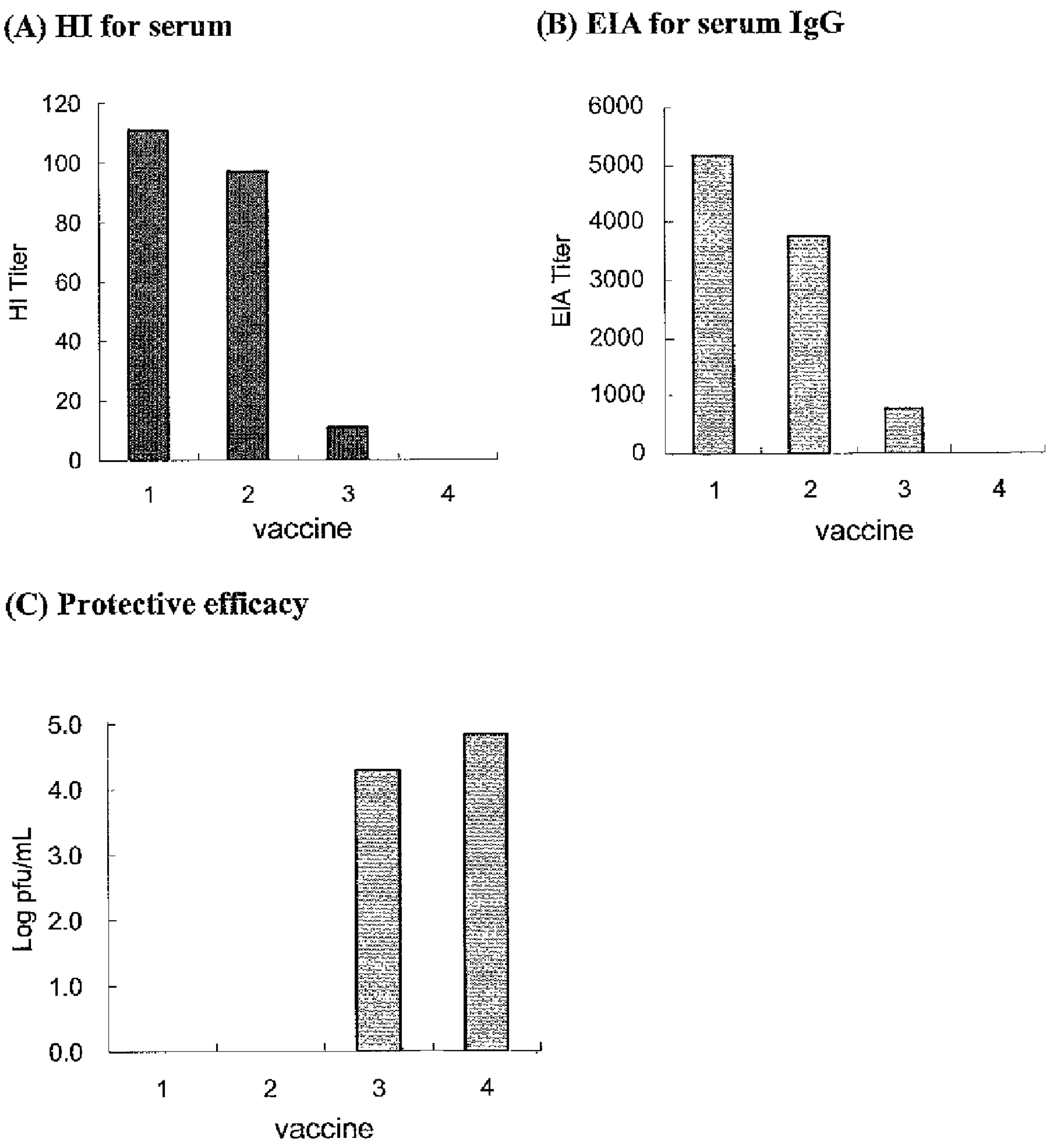
FIG. 13 are graphs showing immunogenicity and protective efficacy of monovalent PT-IV-01re(A/NC)(H1N1) or trivalent (PT-IV-01re(A/NC)(H1N1), PT-IV-01re(A/PA)(H3N2) and B/SD reassortant) vaccine. Reassortant vaccines and mock were given by intranasal route, but inactivated vaccine was injected by subcutaneous route. Hemagglutination inhibition (HI) for serum (a), enzymeimmuno assay (EIA) for serum IgG (b) and protective efficacy of vaccines (c) were performed. 1, PT-IV-01re(A/NC) ($1\times10^{5.5}$ $TCID_{50}$); 2, $1\times10^{5.5}$ $TCID_{50}$ each of trivalent vaccine (PT-IV-01re(A/NC)(H1N1), PT-IV-01re(A/PA)(H3N2) and B/SD reassortant); 3, 3×7.5 ug of HA of inactivated trivalent (A/NC, A/PA, B/SD) split vaccine; 4, Mock.

Protective Efficacy of Trivalent Vaccine Containing A/H1N1, A/H3N2 and B Virus Components We blended three reassortant viruses, PT-IV-01re(A/NC) (H1N1), PT-IV-01re(A/PA)(H3N2) and B/SD reassortant as live trivalent vaccine. Mice were immunized with the trivalent vaccine by i.n. route. Monovalent vaccine PT-IV-01re(H1N1) was included as control. The immunogenicity and protective efficacy from virulent challenge were compared with each other (FIG. 13). In trivalent vaccine formulation (group 2), the level of antibody response was slightly lower than that of monovalent virus vaccine (group 1), and yet was enough to completely clear the virulent virus from infected lung. The protective efficacy of inactivated vaccine was only marginal in trivalent vaccine formula (group 3) and was not enough to clear the virulent virus form the lung as compared to the control without vaccination (group 4). The result shows that PT-IV-01 reassortant vaccine exhibits effective protection in trivalent vaccine formula as well as in monovalent formulation. The results also suggest that multi-valent vaccine formulation could be used for cross-protection against variety of subtypes of influenza viruses.

INDUSTRIAL APPLICABILITY

The present invention relates to an attenuated influenza virus strain and a live vaccine comprising the same. The attenuated influenza virus strain and the live vaccine of the present invention are useful for prevention of seasonal influenza episodes and sudden outbreak of influenza pandemics of predicted or unknown identity, since they have safety, efficacy, high production yield, immediate protection against variety of influenza subtypes and prolonged protection against specific influenza subtype.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the following claims.

We claim:

1. An isolated attenuated influenza virus strain that is PT-IV-01, and that is deposited at Korea Culture Center of Microorganisms (KCCM) under accession number KCCM 10854P, wherein the isolated attenuated influenza strain has an early protection effect against infection at least 3 days post vaccination.

2. A live vaccine comprising the attenuated influenza virus strain of claim 1 as an effective ingredient and at least one pharmaceutically acceptable carrier or excipient.

3. A reassortant influenza virus strain prepared by mating isolated attenuated influenza virus strain PT-IV-01, that is deposited at Korea Culture Center of Microorganisms (KCCM) under accession number KCCM 10854P and that has an early protection effect against infection at least 3 days post vaccination, and other virulent viruses, wherein the reassortant influenza virus strain comprises (i) 6 RNA genomic segments which are originated from the PT-IV-01 attenuated influenza virus strain and which contain internal genes of the PT-IV-01 attenuated influenza virus strain and (ii) 2 RNA genomic segments encoding HA and NA surface antigens of other virulent viruses.

4. The isolated attenuated influenza virus strain according to claim 3, wherein the 6 internal genomic segments have RNA sequences corresponding to the DNA sequences of SEQ ID NOs: 1 to 6.

5. The reassortant influenza virus strain according to claim 3, wherein the other virulent viruses comprise surface antigens in combination of any one selected from H1 to H16 and any one selected from N1 to N9.

6. The reassortant influenza virus strain according to claim 3, wherein the other virulent virus is A/Panama/2007/99 (H3N2).

7. The reassortant influenza virus strain according to claim 3, wherein the other virulent virus is A/New Caledonia/20/99 (H1N1).

8. A live vaccine comprising the reassortant virus strain of claim 3 as an effective ingredient and at least one pharmaceutically acceptable carrier or excipient.

* * * * *

SEQUENCE LISTING

```
<160> NUMBER OF SEQ ID NOS: 18

<210> SEQ ID NO 1
<211> LENGTH: 2295
<212> TYPE: DNA
<213> ORGANISM: Influenza A virus strain PT-IV-01
```

-continued

<220> FEATURE:
<223> OTHER INFORMATION: PB2

<400> SEQUENCE: 1
ttcaatatgg aaagaataaa agaactacga aatctaatgt cgcagtctcg cacccgcgag 60
atactcacaa aaaccaccgt ggaccatatg gccataatca agaagtacac atcaggaaga 120
caggagaaga acccagcact taggatgaaa tggatgatgg caatgaaata tccaattaca 180
gcagacaaga ggataacgga aatgattcct gagagaaatg agcaaggaca aactttatgg 240
agtaaaatga atgatgccgg atcagaccga gtgatggtat cacctctggc tgtgacatgg 300
tggaatagga atggaccaat aacaaataca gttcagtatc caaaaatcta caaaacttat 360
tttgaaagag tcgaaaggct aaagcatgga acctttggcc ctgtccattt tagaaaccaa 420
gtcaaaatac gtcggagagt tgacataaat cctggtcatg cagatctcag tgccaaggag 480
gcacaggatg taatcatgga agttgttttc cctaacgaag tgggagccag gatactaaca 540
tcggaatcgc aactaacgat aaccaaagag aagaaagaag aactccagga ttgcaaaatt 600
tctcctttga tggttgcata catgttggag agagaactgg tccgcaaaac gagattcctc 660
ccagtggctg gtggaacaag cagtgtgtac attgaagtgt tgcatttgac tcaaggaaca 720
tgctgggaac agatgtatac tccaggaggg gaagtgagga atgatgatgt tgatcaaagc 780
ttgattattg ctgctaggaa catagtgaga agagctgcag tatcagcaga tccactagca 840
tctttattgg agatgtgcca cagcacacag attggtggaa ttaggatggt agacatcctt 900
aggcagaacc caacagaaga gcaagccgtg gatatatgca aggctgcaat gggactgaga 960
attagctcat ccttcagttt tggtggattc acatttaaga gaacaagcgg atcatcagtc 1020
aagagagagg aagaggtgct tacgggaaat cttcaaacat tgaagataag agtgcatgag 1080
ggatatgaag agttcacaat ggttgggaga agagcaacag ccatactcag aaaagcaacc 1140
aggagattga ttcagctgat agtgagtggg agagacgaac agtcgattgc cgaagcaata 1200
attgtggcca tggtattttc acaagaggat tgtatgataa aagcagtcag aggtgatctg 1260
aatttcgtca atagggcgaa tcagcgattg aatcctatgc atcaactttt aagacatttt 1320
cagaaggatg cgaaagtgct tttcaaaat tggggagttg aacctatcga caatgtgatg 1380
ggaatgattg ggatattgcc cgacatgact ccaagcatcg agatgtcaat gagaggagtg 1440
agaatcagca aaatgggtgt agatgagtac tccagcacgg agagggtagt ggtgagcatt 1500
gaccgttttt tgagaatccg ggaccaacga ggaaatgtac tactgtctcc cgaggaggtc 1560
agtgaaacac agggaacaga gaaactgaca ataacttact catcgtcaat gatgtgggag 1620
attaatggtc ctgaatcagt gttggtcaat acctatcaat ggatcatcag aaactgggaa 1680
actgttaaaa ttcagtggtc ccagaaccct acaatgctat acaataaaat ggaatttgaa 1740
ccatttcagt ctttagtacc taaggccagt agaggccaat acagtgggtt tgtaagaact 1800
ctgttccaac aaatgaggga tgtgcttggg acatttgata ccgcacagat aataaaactt 1860
cttcccttcg cagccgctcc accaaagcaa agtagaatgc agttctcctc atttactgtg 1920
aatgtgaggg gatcaggaat gagaatactt gtaaggggca attctcctgt attcaactat 1980
aacaaggcca cgaagagact cacagttctc ggaaaggatg ctggcacttt aactgaagac 2040
ccagatgaag gcacagctgg agtggagtcc gctgttctga ggggattcct cattctgggc 2100
aaagaagaca agagatatgg gccagcacta agcatcaatg aactgagcaa ccttgcgaaa 2160
ggagagaagg ctaatgtgct aattgggcaa ggagacgtgg tgttggtaat gaaacggaaa 2220

-continued cgggactcta gcatacttac tgacagccag acagcgacca aaagaattcg gatggccatc 2280
aattagtgtt gaata 2295

<210> SEQ ID NO 2
<211> LENGTH: 2303
<212> TYPE: DNA
<213> ORGANISM: Influenza A virus strain PT-IV-01
<220> FEATURE:
<223> OTHER INFORMATION: PB1

<400> SEQUENCE: 2
ttgaatggat gtcaatccga ccttactttt cttaaaagtg ccagcacaaa atgctataag 60
cacaactttc ccttatactg gagaccctcc ttacagccat gggacaggaa caggatacac 120
catggatact gtcaacagga cacatcagta ctcagaaaag ggaagatgga caacaaacac 180
cgaaactgga gcaccgcaac tcaacccgat tgatgggcca ctgccagaag acaatgaacc 240
aagtggttat gcccaaacag attgtgtatt ggaggcgatg gctttccttg aggaatccca 300
tcctggtatt tttgaaaact cgtgtattga aacgatggag gttgttcagc aaacacgagt 360
agacaagctg acacaaggcc gacagaccta tgactggact ctaaatagaa accaacctgc 420
tgcaacagca ttggccaaca caatagaagt gttcagatca aatggcctca cggccaatga 480
gtctggaagg ctcatagact tccttaagga tgtaatggag tcaatgaaca aagaagaaat 540
ggggatcaca actcattttc agagaaagag acgggtgaga gacaatatga ctaagaaaat 600
gataacacag agaacaatgg gtaaaaagaa gcagagattg aacaaaagga gttatctaat 660
tagagcattg accctgaaca caatgaccaa agatgctgag agagggaagc taaaacggag 720
aacaattgca accccaggga tgcaaataag gggtttgta tactttgttg agacactggc 780
aaggagtata tgtgagaaac ttgaacaatc agggttgcca gttggaggca atgagaagaa 840
agcaaagttg gcaaatgttg taaggaagat gatgaccaat tctcaggaca ccgaactttc 900
tttcaccatc actggagata acaccaaatg gaacgaaaat cagaatcctc ggatgttttt 960
ggccatgatc acatatatga ccagaaatca gcccgaatgg ttcagaaatg ttctaagtat 1020
tgctccaata atgttctcaa acaaaatggc gagactggga aaagggtata tgtttgagag 1080
caagagtatg aaacttagaa ctcaaatacc tgcagaaatg ctagcaagca tcgatttgaa 1140
atatttcaat gattcaacaa gaaagaagat tgaaaaaatc cgaccgctct taatagaggg 1200
gactgcatca ttgagccctg gaatgatgat gggcatgttc aatatgttga gcactgtatt 1260
aggcgtctcc atcctgaacc ttggacaaaa gagatacacc aagactactt actggtggga 1320
tggtcttcaa tcctctgacg attttgctct gattgtgaat gcacccaatc atgaagggat 1380
tcaagccgga gtcgacaggt tttatcgaac ctgtaagcta cttggaatca atatgagcaa 1440
gaaaaagtct tacataaaca gaacaggtac atttgaattc acaagttttt tctatcgtta 1500
tgggtttgtt gccaatttca gcatggagct tcccagtttt ggggtgtctg ggatcaacga 1560
gtcagcggac atgagtattg gagttactgt catcaaaaac aatatgataa acaatgatct 1620
tggtccagca acagctcaaa tggcccttca gttgttcatc aaagattaca ggtacacgta 1680
ccgatgccat agaggtgaca cacaaataca aacccgaaga tcatttgaaa taaagaaact 1740
gtgggagcaa acccgttcca aagctggact gctggtctcc gacggaggcc caaatttata 1800
caacattaga aatctccaca ttcctgaagt ctgcctaaaa tgggaattga tggatgagga 1860
ttaccagggg cgtttatgca acccactgaa cccatttgtc agccataaag aaattgaatc 1920
aatgaacaat gcagtgatga tgccagcaca tggtccagcc aaaaacatgg agtatgatgc 1980

-continued

```
tgttgcaaca acacactcct ggatccccaa aagaaatcga tccatcttga atacaagtca   2040

aagaggagta cttgaggatg aacaaatgta ccaaaggtgc tgcaatttat ttgaaaaatt   2100

cttccccagc agttcataca gaagaccagt cgggatatcc agtatggtgg aggctatggt   2160

ttctagagcc cgaattgatg cacggattga tttcgaatct ggaaggataa agaaagaaga   2220

gttcactgag atcatgaaga tctgttccac cattgaagag ctcagacggc aaaaatagtg   2280

aatttagctt gtccttcatg aaa                                           2303
```

<210> SEQ ID NO 3
<211> LENGTH: 2196
<212> TYPE: DNA
<213> ORGANISM: Influenza A virus strain PT-IV-01
<220> FEATURE:
<223> OTHER INFORMATION: PA

<400> SEQUENCE: 3

```
ccaaaatgga agattttgtg cgacaatgct tcaatccgat gattgtcgag cttgcggaaa     60

aaacaatgaa agagtatggg gaggacctga aaatcgaaac aaacaaattt gcagcaatat    120

gcactcactt ggaagtatgc ttcatgtatt cagattttca cttcatcaat gagcaaggcg    180

agtcaataat cgtagaactt ggtgatccaa atgcactttt gaagcacaga tttgaaataa    240

tcgagggaag agatcgcaca atggcctgga cagtagtaaa cagtatttgc aacactacag    300

gggctgagaa accaaagttt ctaccagatt tgtatgatta caaggagaat agattcatcg    360

aaattggagt aacaaggaga gaagttcaca tatactatct ggaaaaggcc aataaaatta    420

aatctgagaa aacacacatc cacattttct cgttcactgg ggaagaaatg gccacaaagg    480

cagactacac tctcgatgaa gaaagcaggg ctaggatcaa aaccagacta ttcaccataa    540

gacaagaaat ggccagcaga ggcctctggg attcctttcg tcagtccgag agaggagaag    600

agacaattga agaaaggttt gaaatcacag gaacaatgcg caagcttgcc gaccaaagtc    660

tcccgccgaa cttctccagc cttgaaaatt ttagagccta tgtggatgga ttcgaaccga    720

acggctacat tgagggcaag ctgtctcaaa tgtccaaaga agtaaatgct agaattgaac    780

ctttttgaa aacaacacca cgaccactta gacttccgaa tgggcctccc tgttctcagc     840

ggtccaaatt cctgctgatg gatgccttaa aattaagcat tgaggaccca agtcatgaag    900

gagagggaat accgctatat gatgcaatca aatgcatgag aacattcttt ggatggaagg    960

aacccaatgt tgttaaacca cacgaaaagg gaataaatcc aaattatctt ctgtcatgga   1020

agcaagtact ggcagaactg caggacattg agaatgagga gaaaattcca aagactaaaa   1080

atatgaagaa aacaagtcag ctaaagtggg cacttggtga gaacatggca ccagaaaagg   1140

tagactttga cgactgtaaa gatgtaggtg atttgaagca atatgatagt gatgaaccag   1200

aattgaggtc acttgcaagt tggattcaga atgagtttaa caaggcatgc gaactgacag   1260

attcaagctg gatagagctc gatgagattg gagaagatgt ggctccaatt gaacacattg   1320

caagcatgag aaggaattat ttcacatcag aggtgtctca ctgcagagcc acagaataca   1380

taatgaaggg agtgtacatc aatactgcct tgcttaatgc atcttgtgca gcaatggatg   1440

atttccaatt aattccaatg ataagcaagt gtagaactaa ggagggaagg cgaaagacca   1500

acttgtatgg tttcatcata aaaggaagat cccacttaag gaatgacacc gacgtggtaa   1560

actttgtgag catggagttt tctctcactg acccaagact tgaaccacat aaatgggaga   1620

agtactgtgt tcttgagata ggagatatgc ttataagaag tgccataggc caggtttcaa   1680
```

-continued ggcccatgtt cttgtatgtg agaacaaatg gaacctcaaa aattaaaatg aaatggggaa 1740
tggagatgag gcgttgcctc ctccagtcac ttcaacaaat tgagagtatg attgaagctg 1800
agtcctctgt caaagagaaa gacatgacca aagagttctt tgagaacaaa tcagaaacat 1860
ggcccattgg agagtccccc aaaggagtgg aggaaagttc cattgggaag gtctgcagga 1920
ctttattagc aaagtcggta ttcaacagct tgtatgcatc tccacaacta gaaggatttt 1980
cagctgaatc aagaaaactg cttcttgtcg ttcaggctct tagggacaac ctggaacctg 2040
ggacctttga tcttgggggg ctatatgaag caattgagga gtgcctgatt aatgatccct 2100
gggttttgct taatgcttct tggttcaact ccttccttac acatgcattg agttagttgt 2160
ggcagtgcta ctatttgcta tccatactgt ccaaaa 2196

<210> SEQ ID NO 4
<211> LENGTH: 1532
<212> TYPE: DNA
<213> ORGANISM: Influenza A virus strain PT-IV-01
<220> FEATURE:
<223> OTHER INFORMATION: NP

<400> SEQUENCE: 4
gataatcact cactgagtga catcaaaatc atggcgtctc aaggcaccaa acgatcttac 60
gaacagatgg agactgatgg aggacgccag aatgccactg aaatcagagc atccgtcgga 120
aaaatgattg gtggaattgg acgattctac atccaaatgt gcaccgaact caaactcagt 180
gattatgagg gacggttgat ccaaaacagc ttaacaatag agagaatggt gctctctgct 240
tttgacgaaa ggagaaataa ataccttgaa gaacatccca gtgcggggaa agatcctaag 300
aaaactggag gacctatata caggagagta aacggaaagt ggatgagaga actcatcctt 360
tatgacaaag aagaaataag gcgaatctgg cgccaagcta ataatggtga cgatgcaatg 420
gctggtctga ctcacatgat gatctggcat tccaatttga atgatgcaac ttatcagagg 480
acaagagctc ttgttcgcac cggaatggat cccaggatgt gctctctgat gcaaggttca 540
actctcccta ggaggtctgg agccgcaggt gctgcagtca aggagttggg aacaatggtg 600
atggaattgg tcagaatgat caaacgtggg atcaatgatc ggaacttctg gaggggtgag 660
aatggacgaa aaacaagaat tgcttatgaa agaatgtgca acattctcaa agggaaattt 720
caaactgctg cacaaaaagc aatgatggat caagtgagag agagccggaa cccagggaat 780
gctgagttcg aagatctcac ttttctagca cggtctgcac tcatattgag agggtcggtt 840
gctcacaagt cctgcctgcc tgcctgtgtg tatggacctg ccgtagccag tgggtacgac 900
tttgaaaggg agggatactc tctagtcgga atagaccctt tcagactgct tcaaaacagc 960
caagtgtaca gcctaatcag accaaatgag aatccagcac acaagagtca actggtgtgg 1020
atggcatgcc attctgccgc atttgaagat ctaagagtat taagcttcat caaagggacg 1080
aaggtgctcc caagagggaa gctttccact agaggagttc aaattgcttc caatgaaaat 1140
atggagacta tggaatcaag tacacttgaa ctgagaagca ggtactgggc cataaggacc 1200
agaagtggag gaaacaccaa tcaacagagg gcatctgcgg gccaaatcag catacaacct 1260
acgttctcag tacagagaaa tctccctttt gacagaacca ccattatggc agcattcaat 1320
gggaatacag aggggagaac atctgacatg aggaccgaaa tcataaggat gatggaaagt 1380
gcaagaccag aagatgtgtc tttccagggg cggggagtct tcgagctctc ggacgaaaag 1440
gcagcgagcc cgatcgtgcc ttcctttgac atgagtaatg aaggatctta tttcttcgga 1500
gacaatgcag aggagtacga caattaaaga aa 1532

-continued

<210> SEQ ID NO 5
<211> LENGTH: 992
<212> TYPE: DNA
<213> ORGANISM: Influenza A virus strain PT-IV-01
<220> FEATURE:
<223> OTHER INFORMATION: M

<400> SEQUENCE: 5
attgaaagat gagtcttcta accgaggtcg aaacgtacgt actctctatc atcccgtcag 60
gccccctcaa agccgagatc gcacagagac ttgaagatgt ctttgcaggg aagaacaccg 120
atcttgaggt tctcatggaa tggctaaaga caagaccaat cctgtcacct ctgactaagg 180
ggattttagg atttgtgttc acgctcaccg tgcccagtga gcgaggactg cagcgtagac 240
gctttgtcca aaatgccctt aatgggaacg ggatccaaa taacatggac aaagcagtta 300
aactgtatag gaagctcaag agggagataa cattccatgg ggccaaagaa atctcactca 360
gttattctgc tggtgcactt gccagttgta tgggcctcat atacaacagg atggggactg 420
tgaccactga agtggcattt ggcctggtat gtgcaacctg tgaacagatt gctgactccc 480
agcatcggtc tcataggcaa atggtgacaa caaccaatcc actaatcaga catgagaaca 540
gaatggtttt agccagcact acagctaagg ctatggagca aatggctgga tcgagtgagc 600
aagcagcaga ggccatggag gttgctagtc aggctagaca aatggtgcaa gcgatgagaa 660
ccattgggac tcatcctagc tccagtgctg gtctgaaaaa tgatcttctt gaaaatttgc 720
aggcctatca gaaacgaatg gggtgcaga tgcaacggtt caagtgatcc tctcactatt 780
gccgcaaata tcattgggat tttgcacttg acattgtgga ttcttgatcg tctttttttc 840
aaatgcattt accgtcgctt taaatacgga ctgaaaggag ggccttctac ggaaggagtg 900
ccaaagtcta tgagggaaga atatcgaaag gaacagcaga gtgctgtgga tgctgacgat 960
ggtcattttg tcagcataga gctggagtaa aa 992

<210> SEQ ID NO 6
<211> LENGTH: 852
<212> TYPE: DNA
<213> ORGANISM: Influenza A virus strain PT-IV-01
<220> FEATURE:
<223> OTHER INFORMATION: NS

<400> SEQUENCE: 6
aacataatgg atccaaacac tgtgtcaagc tttcaggtag attgctttct ttggcatgtc 60
cgcaaacgag ttgcagacca agaactaggt gatgccccat tccttgatcg gcttcgccga 120
gatcagaaat ccctaagagg aaggggcagt actctcggtc tggacatcaa gacagccaca 180
cgtgctggaa agcagatagt ggagcggatt ctgaaagaag aatccgatga ggcacttaaa 240
atgaccatgg cctctgtacc tgcgtcgcgt tacctaactg acatgactct tgaggaattg 300
tcaagggact ggtccatgct catacccaag cagaaagtgg caggccctct ttgtatcaga 360
atggaccagg cgatcatgga taagaacatc atactgaaag cgaacttcag tgtgattttt 420
gaccggctgg agactctaat attgctaagg gctttcaccg aagagggagc aattgttggc 480
gaaatttcac cattgccttc tcttccagga catactgctg aggatgtcaa aaatgcagtt 540
ggagtcctca tcggaggact tgaatggaat gataacacag ttcgagtctc tgaaactcta 600
cagagattcg cttggagaag cagtaatgag aatgggagac ctccactcac tccaaaacag 660
aaacgagaaa tggcgggaac aattaggtca gaagtttgaa gaaataagat ggttgattga 720

-continued

```
agaagtgaga cacaaactga agataacaga gaatagtttt gagcaaataa catttatgca    780

agccttacat ctattgcttg aagtggagca agagataaga actttctcgt ttcagcttat    840

ttagtactaa aa                                                         852


<210> SEQ ID NO 7
<211> LENGTH: 21
<212> TYPE: DNA
<213> ORGANISM: Artificial Sequence
<220> FEATURE:
<223> OTHER INFORMATION: PB2 sense primer

<400> SEQUENCE: 7

agcgaaagca ggtcaattat a                                                21


<210> SEQ ID NO 8
<211> LENGTH: 18
<212> TYPE: DNA
<213> ORGANISM: Artificial Sequence
<220> FEATURE:
<223> OTHER INFORMATION: PB2 antisense primer

<400> SEQUENCE: 8

agtagaaaca aggtcgtt                                                    18


<210> SEQ ID NO 9
<211> LENGTH: 20
<212> TYPE: DNA
<213> ORGANISM: Artificial Sequence
<220> FEATURE:
<223> OTHER INFORMATION: PB1 sense primer

<400> SEQUENCE: 9

agcgaaagca ggcaaaccat                                                  20


<210> SEQ ID NO 10
<211> LENGTH: 18
<212> TYPE: DNA
<213> ORGANISM: Artificial Sequence
<220> FEATURE:
<223> OTHER INFORMATION: PB1 antisense primer

<400> SEQUENCE: 10

agtagaaaca aggcattt                                                    18


<210> SEQ ID NO 11
<211> LENGTH: 19
<212> TYPE: DNA
<213> ORGANISM: Artificial Sequence
<220> FEATURE:
<223> OTHER INFORMATION: PA sense primer

<400> SEQUENCE: 11

agcgaaagca ggtactgat                                                   19


<210> SEQ ID NO 12
<211> LENGTH: 18
<212> TYPE: DNA
<213> ORGANISM: Artificial Sequence
<220> FEATURE:
<223> OTHER INFORMATION: PA antisense primer

<400> SEQUENCE: 12

agtagaaaca aggtactt                                                    18
```

-continued

```
<210> SEQ ID NO 13
<211> LENGTH: 15
<212> TYPE: DNA
<213> ORGANISM: Artificial Sequence
<220> FEATURE:
<223> OTHER INFORMATION: NP sense primer

<400> SEQUENCE: 13

agcaaaagca gggta                                                      15


<210> SEQ ID NO 14
<211> LENGTH: 18
<212> TYPE: DNA
<213> ORGANISM: Artificial Sequence
<220> FEATURE:
<223> OTHER INFORMATION: NP antisense primer

<400> SEQUENCE: 14

agtagaaaca agggtatt                                                   18


<210> SEQ ID NO 15
<211> LENGTH: 17
<212> TYPE: DNA
<213> ORGANISM: Artificial Sequence
<220> FEATURE:
<223> OTHER INFORMATION: M sense primer

<400> SEQUENCE: 15

agcgaaagca ggtagat                                                    17


<210> SEQ ID NO 16
<211> LENGTH: 18
<212> TYPE: DNA
<213> ORGANISM: Artificial Sequence
<220> FEATURE:
<223> OTHER INFORMATION: M antisense primer

<400> SEQUENCE: 16

agtagaaaca aggtagtt                                                   18


<210> SEQ ID NO 17
<211> LENGTH: 20
<212> TYPE: DNA
<213> ORGANISM: Artificial Sequence
<220> FEATURE:
<223> OTHER INFORMATION: NS sense primer

<400> SEQUENCE: 17

agcaaaagca gggtgacaaa                                                 20


<210> SEQ ID NO 18
<211> LENGTH: 18
<212> TYPE: DNA
<213> ORGANISM: Artificial Sequence
<220> FEATURE:
<223> OTHER INFORMATION: NS antisense primer

<400> SEQUENCE: 18

agtagaaaca agggtgtt                                                   18
```